United States Patent [19]
Binns et al.

[11] Patent Number: 5,182,210
[45] Date of Patent: Jan. 26, 1993

[54] FOWLPOX VIRUS PROMOTERS

[75] Inventors: Matthew M. Binns, Huntingdon; Michael E. G. Boursnell, Huntingdon; Joan I. A. Campbell, Huntington; Fiona M. Tomley, Cambridge, all of England

[73] Assignee: National Research Development Corporation, London, United Kingdom

[21] Appl. No.: 469,608

[22] PCT Filed: Oct. 21, 1988

[86] PCT No.: PCT/GB88/00922

§ 371 Date: Apr. 17, 1990

§ 102(e) Date: Apr. 17, 1990

[87] PCT Pub. No.: WO89/03879

PCT Pub. Date: May 5, 1989

[30] Foreign Application Priority Data

Oct. 23, 1987 [GB] United Kingdom ................. 8724885

[51] Int. Cl.$^5$ ...................... C12N 15/63; C12N 15/86; C12N 15/11
[52] U.S. Cl. ................. 435/320.1; 536/24.1; 435/235.1; 435/69.1; 935/6; 935/34
[58] Field of Search ................. 435/320.1, 172.3, 69.1, 435/235.1, 240.2; 536/27; 935/6, 8, 32, 34, 36, 57, 65, 70; 424/89

[56] References Cited

FOREIGN PATENT DOCUMENTS

| 0227414 | 7/1987 | European Pat. Off. |
| 0284416 | 9/1988 | European Pat. Off. |
| 8600528 | 1/1986 | PCT Int'l Appl. |
| 8605806 | 10/1986 | PCT Int'l Appl. |
| 8802022 | 3/1988 | PCT Int'l Appl. |
| 9002191 | 3/1990 | PCT Int'l Appl. |

OTHER PUBLICATIONS

Andrewes, C. et al. 1978, *Viruses of Vertebrates*, pp. 358, 373 Cassell & Co. Ltd., London.

(List continued on next page.)

Post, L. et al. 1981, *Cell* vol. 25, pp. 227–232.

*Primary Examiner*—Richard A. Schwartz
*Assistant Examiner*—Mary E. Mosher
*Attorney, Agent, or Firm*—Nixon & Vanderhye

[57] ABSTRACT

Fowlpox virus (FPV) promoter DNA for use in expressing a foreign gene inserted in a FPV vector by homologous recombination, which comprises the promoter of any of the following FPV genes:

(1) The FB4b gene which encodes a protein of about 657 amino acids in a sequence beginning Met Glu Ser Asp Ser Asn Ile Ala Ile Glu
    Glu Val Lys Tyr Pro Asn Ile Leu Leu Glu;

(2) The BamHI fragment ORF8 gene encoding a protein of about 116 amino acids in a sequence beginning Met Glu Glu Gly Lys Pro Arg Arg Ser Ser
    Ala Val Leu Trp Met Leu Ile Pro Cys Gly;

(3) The BamHI fragment ORF5 gene encoding a protein of about 105 amino acids in a sequence beginning Met Ile Ile Arg Arg Asn Asn Lys Ala Leu
    Gly Ser Val Met Ser Asp Phe Ile Lys Thr; and (4) The BamHI fragment ORF10 gene encoding a protein of about 280 amino acids in a sequence beginning Met Lys Phe Lys Glu Val Arg Asn Thr Ile
    Lys Lys Met Asn Ile Thr Asp Ile Lys Ile.

8 Claims, 4 Drawing Sheets

OTHER PUBLICATIONS

Taylor, et al "Fowlpox Virus Based Recombinant Vaccines" Technological Advances in Vaccine Develop. 1988, pp. 321-334.
Wild et al "Fowlpox Virus Recombinant..." Vaccine, vol. 8 Oct. 1990, 441.
Ogawa et al "Recombinant Fowlpox Viruses..." Vaccine, vol. 8 Oct. 1990, p. 486.
Buller, R. M. L. et al. 1985. *Nature*, vol. 317, pp. 813-815.
Coupar, B. E. H. et al. 1986. *Eur. J. Immunol., vol. 16, pp. 1479-1487.*
Panicali, D. et al. 1986. *Gene*, vol. 47, pp. 193-199.
Shepard, B. et al. 1987. *Plasmid, vol. 18, pp. 16-23.*
Boyle, D. B. et al. 1986. *J. Gen Virol.*, vol. 67. pp. 1591-1600.
M. Mackett & G. Smith, J. Gen. Virol., 67, 2067-2082 (1986).
M. Kieny et al, Nature, 312, 163-166 (1984).
M. M. Binns et al, Israel. J. Vet. Med., 42, 124-127 (1986).
S. Venkatesan et al, Cell, 125, 805-813 (1981).
M. A. Cochran et al, J. Virol., 54, 30-37 (1985).
C. Bertholet et al, Proc. Natn. Acad. Sci., U.S.A., 82, 2096-2100 (1985).
J. P. Weir, Virology, 158, 206-210 (1987).
D. Panicali et al, Proc. Natn. Acad. Sci., U.S.A., 80, 5364-5368 (1983).
B. Coupar, J. Gen Virol., 68, 2299-2309 (1987).
J. Rosel et al, J. Virol., 56, 830-838 (1985).
M. Perkus et al, Science, 229, 981-984 (1985).
J. P. Weir et al, J. Virol., 61, 75-80 (1987).
D. Boyle et al, Virology, 156, 355-365 (1987).
A. Plucienniczak et al, Nucleic Acid Research, 13, 985-988 (1985).
F. M. Tomley talk at International Poxvirus Workshop, Cold Spring Harbour, N.Y. Apr. 24-28, 1986.
J. Campbell poster at Soc. Gen Microbiol., Sep. 1987.
F. M. Tomley et al, J. Gen Virol., 69, 1025-1040 (1988).
M. Boursnel poster at VII International Poxvirus/Iridovirus Meeting, Heidelberg, Aug. 1988.

- Foreign gene
- Promoter
- Non-essential region
- Multiple cloning site
- Plasmid DNA Selected on Xgal amp. plates

FOWLPOX VIRUS PROMOTERS

BACKGROUND OF THE INVENTION

1. Field of the Invention

The invention is in the field of recombinant DNA technology and relates to promoters useful for the expression of foreign DNA inserted into a fowlpox virus vector.

2. Description of the Prior Art

Poxviruses are large viruses with a complex morphology containing linear double-stranded DNA genomes. They are among the few groups of DNA viruses that replicate within the cytoplasm of the cell. They are subclassified into six genera: orthopoxviruses, avipoxviruses, capriopoxviruses, leporipoxviruses, parapoxviruses and entomopoxviruses. Vaccinia virus, an orthopoxvirus, is the most widely studied of the poxviruses, and is the subject of U.S. Pat. No. 4,603,112 (Paoletti et al.,). Fowlpox virus is an avipoxvirus or avian poxvirus.

Recent advances in recombinant DNA technology have allowed vaccinia virus to be used as a vector to carry and express foreign genes. For a review see M. Mackett & G. L. Smith, Journal of General Virology 67, 2067-2082 (1986). Certain properties of vaccinia virus make it suitable for this purpose. Firstly, it tolerates large amounts of extra DNA in its genome, at least up to 25,000 base pairs. Secondly, it encodes its own RNA polymerase which specifically initiates transcription of messenger RNA, beginning at the viral promoter sequences on the DNA genome. The host cell RNA polymerase II does not recognise these viral promoters, nor does the vaccinia RAN polymerase transcribe from promoters recognised by the host cell RNA polymerase. These two properties allow foreign genes to be inserted into the vaccinia virus genome under the control of a vaccinia virus promoter. Because of the very large size of the vaccinia virus genome (186,000 base pairs) and the fact that the DNA alone is not infectious, conventional recombinant DNA techniques of restriction enzyme cleavage and ligation of DNA fragments into the genome are not technically feasible. Therefore DNA is introduced into the genome by a process of homologous recombination. Homologous recombination involves essentially (1) pre-selecting a length of the vaccinia virus (VV) genome in some region which does not impair the replication and normal functioning of the virus (hereinafter called a "non-essential region"), (2) making a construct of a length of foreign DNA in a copy of the non-essential region so that the foreign DNA is flanked by extensive sequences of non-essential region of VV DNA, (3) co-infecting appropriate tissue culture cells with the VV and the construct and (4) selecting cells containing VV in which the pre-selected length has been swapped over ("recombined") in vivo so that it is replaced in the genome by the construct DNA.

In order to insert the foreign gene in to the construct, the construct should itself be contained in a vector, e.g. a plasmid. It should also comprise a promoter for regulating expression of the foreign DNA within the virus. The procedure is more fully described in the Mackett and Smith review supra. Vaccinia virus vectors have been used in this way experimentally for the expression of DNA for several viral proteins. See, for example, M. Kieny et al., Nature 312, 163-166 (1984) on the expression of a rabies virus glycoprotein. Since the vaccinia virus vector can be attenuated, i.e. altered to make it less virulent, without impairing its use as a vector, it has considerable potential for use in vaccination.

It has been recognised for some years that in principle similar technology could be applied to fowlpox virus (FPV), see, for example, M. M. Binns et al., Israel Journal of Veterinary Medicine 42, 124-127 (1986), thereby providing a vector for use in vaccinating poultry. FPV like VV, has a genome of vast size (it is even larger than VV: estimates range from 240 to 360 kilobases) and it is not known to what extent it is similar to vaccinia virus.

One of the essential requirements for the expression of foreign DNA in a FPV vector is a strong promoter, which will be recognised by the FPV RNA polymerase. Several promoters have been identified in VV but their relative strengths have not been fully explored. The main ones are as follows:

1. p7.5. The 7.5 Kd polypeptide promoter, which has early and late activities, has been widely used to express genes inserted into vaccinia, S. Venkatesan et al., Cell 125, 805-813 (1981), M. A. Cochran et al., J. Virol. 54, 30-37 (1985).

2. p11. The gene for the 11 Kd major structural polypeptide, mapping at junction of vaccinia HindIII fragments F/E, has late promoter which has been widely used, C. Bertholet et al. Proc. Natl. Acad. Sci. USA 82, 2096-2100, (1985).

3. pTK. Promotes the thymidine kinase, gene which maps in vaccinia HindIII fragment J, J. P. Weir et al., Virology 158 206-210 (1987). This promoter has not been used much and is thought not to be strong.

4. pF. Promotes an unknown, early, non-essential gene, which maps in vaccinia HindIII fragment F, see D. Panicali et al. Proc. Natl. Acad. Sci. USA 80, 5364-5368 (1983). It has recently shown to be "relatively inefficient" i.e. 10-fold lower than the TK promoter, B. E. H. Coupar et al., J. Gen. Virol. 68, 2299-2309 (1987).

5. p4b. The 4b gene encodes a 62 Kd core protein. It has a late promoter which maps in vaccinia HindIII fragment A, see J. Rosel et al., J. Virol. 56, 830-838 (1985). The 4b protein accounts for approx 10% of viral protein in vaccinia.

6 and 7. pM. and pI. These are two uncharactised early vaccinia promoters from vaccinia HindIII M and I fragments respectively used in construction of a multivalent vaccinia vaccine, M. E. Perkus et al., Science 229, 981-984 (1985).

8. p28K. Promotes a gene encoding a later 28 Kd core protein, J. P. Weir et al., J. Virol. 61, 75-80 (1987). It hasn't been used much.

Because of the lack of information about the genomic DNA sequence of FPV (and, indeed, VV, since only about a third of the genomic DNA sequence of VV has been published), it has not been possible to predict whether a particular promoter known in VV has a counterpart in FPV, nor could its efficiency as a promoter be predicted.

Only very limited data have been published about the DNA sequence of the FPV genome. Thus, D. B. Boyle et al., Virology 156, 355-365 (1987), have published the sequence of the thymidine kinase (TK) gene and flanking sequence totalling 1061 base pairs. These authors looked at the FPV TK promoter region and noted that it contained a so-called consensus sequence common to eleven VV gene promoters [A. Plucienniczak et al., Nucleic Acids Research 13, 985-988 (1985)]. This "consensus sequence" is supposedly based on TATA—(20 to 24 bp)—AATAA, but there were many divergences from it and the whole region is so AT-rich that the notion of a "consensus sequence" does not bear critical examination. Moreover, the distances between these consensus sequences and the 5' ends of the TK mRNAS differed as between FPV and VV. Since the FPV TK gene was found to be expressed in vaccinia virus vector, and therefore recognised by the VV RNA polymerase, some degree of similarity between these two promoters is deducible. It does not follow, of course, that every VV promoter would be highly homologous with every FPV promoter and indeed unpublished data of the present inventors suggests that this is not the case.

Further prior art is referred to below after the section "Summary of the Invention", without which its context would not be apparent.

SUMMARY OF THE INVENTION

Much of the present invention has arisen by locating some FPV genes, testing the 5'-non-coding region associated with them for promotional strength and thereby selecting certain strong promoters.

Several regions of the FPV genome have been investigated in research leading to the invention. One of them arises by cutting the DNA with the enzyme BamHI, selecting from a range of plasmids thereby generated one with an insert of about 11.2 kilobases and examining that length of DNA. Another arose by random cloning of the FPV genome and comparing these sequences with that of DNA of the vaccinia 4b gene mentioned above.

As a result, four strong promoters have been found and the invention provides various DNA molecules containing them. The science of promoters of poxvirus DNA is at present poorly understood. It is known that certain regions to the 5' or "upstream" end of a gene serve to assist in transcribing genomic DNA into messenger RNA by binding the RNA polymerase involved in the transcription so that the mRNA which contains the start codon of the gene can be transcribed. Such upstream regions are referred to as the "promoter". It is often not possible to say for certain which nucleotides of the upstream sequence are essential and which are inessential for promotion, nor is the minimum or maximum length of the promoter known with great precision. Although this lack of precision in the whereabouts and length of the promoter might at first sight seem rather unsatisfactory, it is knot a problem is practice since there is normally no harm in including additional DNA beyond the region which serves to transcribe the DNA. Further as described later, it is possible by tedious experiment to determine this region more precisely. In all these circumstances, it is therefore more appropriate to define the promoter by reference to the gene which it precedes, rather than by reference to the sequence of the promoter. The genes in question are those of open-reading frames ORF8, ORF5 and ORF10 of the BamHI fragment and the gene of FPV which most nearly corresponds to (is of highest homology with) the vaccinia 4b gene. The last-mentioned FPV gene is conveniently designated FP4b. These genes are fully identified hereinafter in Example 1.

These genes can be defined in various ways, always remembering, of course, that there will doubtless be minor differences in their sequence between one strain or type of FPV and another. One convenient, arbitrary, way of defining them is by reference to an appropriate length of the amino acid sequence which they encode. It may reasonably be assumed that the first 10 or, more preferably, the first 20 amino acids, say, would form a unique sequence in FPV. Accordingly, one convenient definition of four of the genes is based on the first 20 amino acids as follows:

(1) The FP4b gene which encodes a protein of about 657 amino acids in a sequence beginning Met Glu Ser Asp Ser Asn Ile Ala Ile Glu
Glu Val Lys Tyr Pro Asn Ile Leu Leu Glu (2) The BamHI fragment ORF8 gene encoding a protein of about 116 amino acids in a sequence beginning Met Glu Glu Gly Lys Pro Arg Arg Ser Ser
Ala Val Leu Trp Met Leu Ile Pro Cys Gly (3) The BamHI fragment ORF5 gene encoding a protein of about 105 amino acids in a sequence beginning Met Ile Ile Arg Arg Asn Asn Lys Ala Leu
Gly Ser Val Met Ser Asp Phe Ile Lys Thr (4) The BamHI fragment ORF10 gene encoding a protein of about 280 amino acids in a sequence beginning Met Lys Phe Lys Glu Val Arg Asn Thr Ile
Lys Lys Met Asn Ile Thr Asp Ile Lys Ile In relation to the genes, it will be appreciated, of course, that variations in the 20 amino acids are likely to occur between different FPV strains. Probably there would be at least 90% homology over the whole gene, but there may well be less homology over the first 20 amino acids, perhaps up to 3 or 4 differences. It is confidently believed however that no one skilled in the field will be in any doubt as to which gene is intended, whatever the precise degree of aberration in the amino acid sequence of the first 10 or 20.

It is expected that before long it will be possible to create a partial map of the FPV genome. FPV, like other poxviruses, has a linear genome with similarities between its ends: The terminal sequences are invertedly repeated. Within these terminal inverted repeats (TIRs) there are tandemly repeated sequences. The BamHI digest gave rise to clones containing these terminal inverted repeat (TIR) sequences and it has been determined that a length of about 3.7 to 4.0 kb at one end of the approximately 11.2 kb fragment (the left-hand of the sequence thereof shown hereinafter) lies within a TIR in the strain of FPV investigated. The FP4b gene is believed to lie in a central region of the genome. The whereabouts of the 0.79 kb sequence is unknown at present.

The invention includes a DNA molecule which consists substantially of the non-coding DNA to the 5'-end of each of the above-identified genes and comprising the promoter thereof. "Non-coding" means not coding for that gene : it could code for another gene as well as serving as a promoter. Any reasonable length of such DNA, typically up to 150, usually up to 100, and especially up to 80 nucleotides (or base-pairs in the case of ds DNA) of the 5'-end (even if it codes for DNA within the next gene along the genome), is herein referred to as "promoter DNA".

The invention also includes a recombination vector comprising a cloning vector containing a non-essential region (NER) sequence of FPV, said NER being interrupted by DNA which consists of or includes (a) promoter DNA of the invention, followed by (b) a foreign gene (i.e. a gene which it is desired to insert into the FPV vector) transcribable by the promoter.

In one particular aspect, the invention includes a recombination vector which comprises in order:
(1) a first homologously recombinable sequence of the fowlpox virus (FPV) genome,
(2) a sequence within a first portion of a non-essential region (NER) of the FPV genome,
(3) FPV promoter DNA according to the invention,
(4) a foreign gene transcribably downstream of the promoter (whereby when the fowlpox virus RNA polymerase binds to the promoter it will transcribe the foreign gene into mRNA) and
(5) a sequence within a second portion of the same NER of the FPV genome, the first and second sequences preferably being in the same relative orientation as are the first and second portions of the NER within the FPV genome, and
(6) a second homologously recombinable sequence of the FPV genome, said sequences (1) and (6) flanking the NER in the FPV genome and being in the same relative orientation in the recombination vector as they are within the FPV genome.

In another aspect, the invention includes a DNA construct which comprises a promoter of the invention transcribably linked to a foreign gene. Such a construct or "cassette" can be inserted in a cloning vector, which can then be used as a recombinant vector useful in preparing a recombination vector of the invention.

The invention further includes hots harbouring the recombination and recombinant vectors of the invention, especially a bacterial hot harbouring a plasmid vector.

The invention is further directed to a recombinant FPV which is the product of homologous recombination of FPV with a recombination vector of the invention containing a foreign gene; the process of homologous recombination; animal cells infected with such a recombinant FPV; a process of in vitro culture of these infected cells; and a method of vaccinating a responsive animal, especially a chicken, which comprises inoculating it with the recombination vector of the invention.

Further Description of the Prior Art

At the International Poxvirus Workshop meeting held of Cold Spring Harbor, New York, on Sep. 24-28, 1986, F. M. Tomley gave a talk, with slides, entitled "Molecular structure and organisation of an 11.3 kb fragment of fowlpoxvirus". This talk presented an outline of the preliminary results of sequencing the 11.2 kb BamHI fragment (at that time thought to be 11.3, rather than 11.2 kb long). The talk dealt with the AT richness of the fragment, included a slide showing 20 open reading frames, discussed codon usage in FPV, compared the FPV 48 kd predicted polypeptide (herein "ORF 1") with a 42 kd early protein in VV and compared other predicted polypeptides with hepatic lectins and anti-alpha-trypsinogen. No mention was made of the functionality of the ORFs or of the strength of gene expression, nor was any length of DNA sequence shown. The same talk was given at the Herpes/Poxvirus Workshop of the Society for General Microbiology, held at St. Andrews, Scotland, Apr. 1987.

At the corresponding meeting in September 1987, J. I. A. Campbell et al., displaced a poster relating the terminal BamHI fragment of FPV, lying between the 11.2 kb BamHI fragment and the end of the genome. No DNA sequence was shown.

During the priority year, F. M. Tomley et al., J. Gen. Virology 69, 1025-1040 (1988), have given the full sequence of the BamHI fragment, together with some detail of relationships of predicted polypeptides to other proteins. A study of the functional promoter activity of the sequences upstream of the 12 major ORFs is referred to as unpublished data. The first disclosure of this data was in a poster exhibited by M. E. G. Boursnell et al., at the VIIth International Poxvirus/Iridovirus Meeting, Heidelberg, Aug. 22-26 1988.

BRIEF DESCRIPTION OF THE ACCOMPANYING DRAWINGS

DESCRIPTION OF THE PREFERRED EMBODIMENTS

Figure 1:
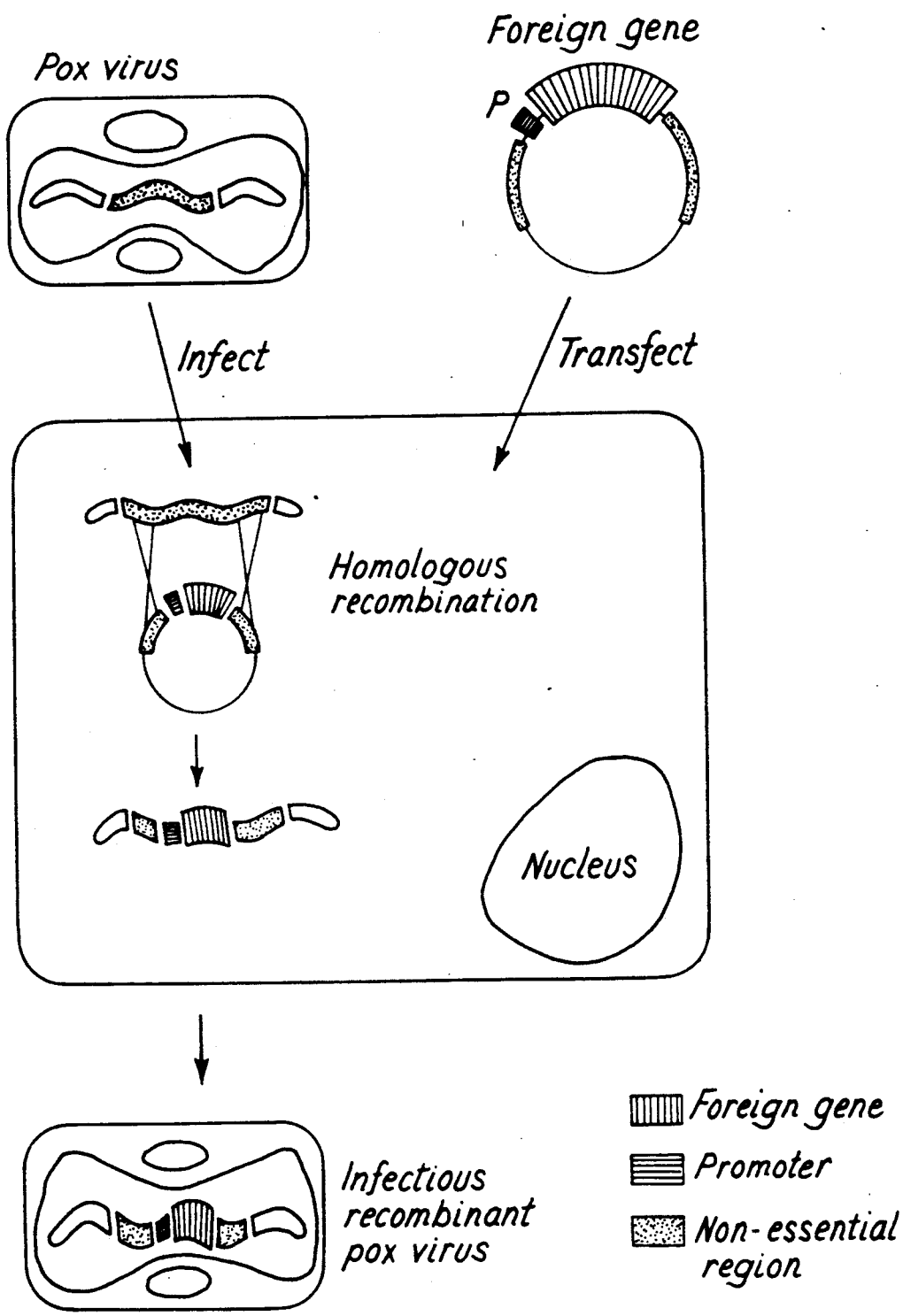
FIG. 1 shows the general scheme of a procedure of homologous recombination as applied to fowlpox virus.

While the precise length of DNA required for promotion is not known, it is generally reckoned to be up to 100 base pairs from the RNA start site, but this can be as much as 50 base pairs away from the gene start site (the ATG codon). Accordingly a DNA sequence contained within 150 base pairs, less preferably 100 or even 80 bp. to the 5'-end of the gene (immediately preceding the start codon) is of particular interest for the purposes of the invention. The DNA sequences of these 150 base pairs are shown below (arbitarily divided into blocks of 10 for ease of reading) for genes (1) to (4).

```
FP4b (5')   TATTACGTGG ATAAATATAT ATCTTCAGGA AAAGGGTATT ATGTTACCAG
            ATGATATAAG AGAACTCAGA GATGCTATTA TTCCTTAACT AGTTACGTCT
            CTTTAGGTAC TTATTTTGAT ACGTTACAAG TAAAAAACTA TCAAATATAA
                                                                (3')

ORF8 (5')   AGAATAGCAT TGCAAAGTTC TACACGATCC ATTGTATAAT ATAGGTGTTC
            AACACCTCTC GATATATCAT TATTTGTTTT TTCAATTTTA TTATAAGTAG
            TTTGAATGCA TTTTTAAGTT TAATAAATCT TGATAAAGTA TATTTAAAAA
                                                                (3')

ORF5 (5')   TAAACCAAAT ATACTAAAAT ATAAAATTAT GCCGCGGGAT GATAAGATAC
            TTCAGATGAT CGTGATGAAC TATATTTATT AATTGGCAAT ACTTAAAAAT
            AATGTTTATA ACATATGTAA ATATAATAAA CAATAATTTA GATTTTTAAA
                                                                (3')
```

```
ORF10 (5')  ACTAGATTGT ACAAATATTA ATATGTGTAA TTTCTTATAT AGTAATATAG
            TAGGATGTGA TATATGCACC ATAGAAAAAT TTTATATTTG TATAAAACCG
            ATAAATAAAA TAAACTTATT TAGTTACTTT GTAGAGTATA CTAAATAATA
                                                                  (3')
```

In the above sequences an ATG start codon follows on at the right-hand or 3'-end.

Just how much of the 5'-non-coding sequence is necessary for efficient promotion is not known precisely. However, experiments can be carried out to answer this question, and in fact some have been performed for VV. Consequently, similar experimentation would be possible to determine the sequences necessary for FPV. One such technique is deletion mapping: by the simple expedient of removing parts of the sequence under test, and assaying its subsequent promotion efficiency, the sequences sufficient for promoter activity can be identified. Thus, in vaccinia it has been found that 100 base pairs (bp) of sequence upstream of the 11 kilodalton (11Kd) gene are sufficient to act as a promoter and temporally regulate late transcription C. Bertholet et al., Proc. Natl. Acad. Sci. (USA) 82 2096–2100 (1985). Deletions leaving about 15 bp on the 5'-side of the putative site at which mRNA transcription starts still yielded high levels of expression, C. Bertholet et al., EMBO Journal 5, 1951–1957 (1986). However, M Hanggi et al., EMBO Journal 5 1071–1076 (1986) found that the same fragment functioned at a lower level when it was translocated to a new position. At this new position, deletions leaving 32 bp on the 5'-side of the ATG start codon had no effect on promoter strength. M. A. Cochran et al., Proc. Natl. Acad. Sci (USA) 82, 19–23 (1985) showed that the activity of the 7.5Kd VV promoter resided in an approximately 30 bp segment. J. P. Weir and B. Moss, Virology 158, 206–210 (1987) found that 32 bp upstream of the RNA start site were sufficient for correctly regulated promotion of the thymidine kinase (TK) gene in VV.

A 228 bp sequence of DNA from in front of a 28Kd late gene (from positions −218 to +10 relative to the RNA start site) was placed in front of the chloramphenicol acetyltransferase (CAT) gene and found to act as a promoter, J. P. Weir and B. Moss, J. Virology 61, 75–80 (1987). A series of 5' deletions extending towards the RNA start site were made. A gradual reduction in CAT expression occurred as the deletions extended from −61 to −18. Mutants that retained 18 bp before and 10 bp after the RNA start site still expressed the CAT gene as a late gene, though at a submaximal level.

While deletion mapping can define those sequences sufficient for promotion activity, it cannot pinpoint the exact bases necessary for activity within the defined sequences. Various workers have altered bases within putative promoter sequences, either by synthesising specific oligonucleotides, J. Hanggi et al., loc. cit., or by site-directed mutagenesis, J. P. Weir and B. Moss. J. Virology 61, 75–80 (1987). In both cases alternations in very few, even single, bases had profound effects on the efficiency of promotion, and hence individual bases of importance could be identified. Since, however, some changes in sequence are permissible without loss of the promotional effect, it will be appreciated that it is necessary that the invention should cover sequences which are variant, by substitution as well as by deletion or addition from the non-coding sequences of length up to 150 bp referred to above.

The recombination vector could contain additional sequence to that herein referred to as promoter DNA. Additional sequence could comprise (a) additional sequence more than 150 bp 5'-ward from the ATG initiation codon, (b) sequence inserted into the 150 bp without destroying promoter activity or (c) part of the sequence of the FPV gene (inclusive of the ATG initiation codon and onwards), e.g. up to 100 bp thereof.

The above experiments require testing for the efficiency of the promoter. It is not necessary for this purpose to introduce a promoter-gene construct into FPV and monitor expression of the gene product. A shorter method, known as transient assay, is known for use with VV, M. A. Cochran et al., Proc. Natl. Acad. Sci. (USA) 82, 19–23 (1985). in transient assay, the promoter is linked to a gene with an easily assayable product. A plasmid containing this construct is then introduced into a cell which has been infected with the virus. The viral RNA polymerase can transcribe off the promoter, even though the promoter has not been incorporated in the viral genome. Because expression only lasts while both the virus and the plasmid DNA are present in the cell together, this form of expression is known as 'transient'. Two different marker genes have been used in vaccinia virus transient assay systems, the chloramphenicol acetyltransferase (CAT) gene, M. A. Cochran et al., supra of the beta-galactosidase "lacZ" gene, D. Panicali et al., Gene 47 193–199 (1986). using the CAT gene the promoter sequences under test were cloned in front of a complete CAT gene which included its own ATG start codon. Thus, this is a "transcriptional fusion" sequence, i.e. the sequences are fused in a non-coding region. In the case of the beta-galactosidase lacZ gene both a transcriptional and a translational fusion vector were described, both for transient assay and for testing in recombinants. The translational fusion vector contained a beta-galactosidase gene lacking its own start codon, so that the fusion occurs within a coding region. The ATG start codon was provided by the VV promoter under test. The beta-galactosidase "lacZ" gene was therefore cloned so as to be in frame with the VV gene start codon, the VV gene being fused to the lacZ gene before codon 9 of the latter. Thus, the promoter was in exactly the same context relative to the initiation codon used in the fusion vector as in its native position.

In the present invention, the lacZ gene has been used only for the transient assay to determine promoter strength. It will be appreciated, however, that in the practice of the invention a foreign gene relevant to improving the condition of poultry would be inserted into the fowlpox virus. Preferably the gene will be one appropriate to an in vivo sub-unit vaccine, for example one or more genes selected from Infectious Bonchitis Virus (IBV), Infectious Bursal Disease virus, Newcastle Disease Virus (NDV), Marek's disease virus, infectious laryngotracheitis virus and genes encoding antigenic proteins of Eimeria species. Particular genes of interest are the spike genes of IBV and the HN and F genes of NDV as described in PCT Patent Application Publication No. WO 86/05806 and European Patent Application Publication No. 227414A (both National Research Development Corporation). In order for the foreign gene to be correctly translated in vivo it is necessary for the foreign gene to have its own ATG start codon inserted in the region just following the promoter.

It is necessary to locate a non-essential region of the FPV, in which to insert the promoter of the invention and the desired foreign gene. In principle, they could be inserted anywhere in the FPV genome which would not harm the basic functions of the virus, or interfere with the action of the FPV promoter or the foreign gene. It can be a coding or non-coding region. In VV-, the thymidine kinase (TK) gene has often been used for this purpose. See, for instance, Example 4 of WO 86/05806 mentioned above, which describes the expression of the IBV spike gene in VV using the 7.5K vaccinia promoter and the TK non-essential region.

It will be appreciated that the detection of the insertion of the foreign gene would depend on detection of virally infected cells which do not produce any of the non-essential gene, e.g. TK. Such cells are described as "TK minus". Alternatively, one could use the TK gene or a markerless coding or non-coding region and detect the insertion of the foreign gene by a hybridisation assay in which a labelled nucleotide sequence complementary to the foreign gene sequence is employed.

PCT Application WO 88/02022 published Mar. 24, 1988 (CSIRO) describes a method of stably inserting a foreign gene within the TK gene of FPV, with the aid of a dominant selectable marker gene ("Ecogpt") and a VV promoter. The disclosure of this patent application can be used in the present invention, with substitution of an FPV promoter of the invention for the VV promoter. Use of the FPV promoter is favoured as likely to be more acceptable to the veterinary medicine licensing authorities.

The promoter of the invention and foreign gene than have to be inserted into the non-essential region (NER) of the FPV genome. The procedure of homologous recombination illustrated by FIG. 1 of the drawings, provides a way of doing so. A fragment of genomic DNA containing the NER is sub-cloned in a cloning vector. If desired, it can be shortened to remove most of the sequence flanking it. A construct is then made, in the cloning vector, comprising part of the NER (starting at one end thereof), followed by the FPV promoter ("P") of the invention, followed by the foreign gene, followed by substantially the remainder of the NER (terminating at the other end thereof). This construct, in an appropriate vector, forms the recombination vector which is used to transfect the cells infected with the FPV, e.g. by the calcium phosphate method, whereby recombination occurs between the NER sequences in the vector and the NER sequences in the FPV. The FPV then automatically re-packages this altered genome and the thus altered FPV (recombinant FPV) is part of this invention.

FIGS. 2 and 3 of the drawings illustrative alternative methods of making the above recombination vector. Referring first to FIG. 2, a non-essential region possessing two restriction sites A, B is inserted in an appropriate vector, which, by way of illustration only, will be described as a plasmid. In another plasmid having the same (or ligatably compatible) restriction sites A, B, a construct is made of FPV promoter sequence of the invention followed by the foreign gene sequence. It is of course essential that this construct is made so that the mRNA transcription will begin at or before the start codon of the foreign gene. Since it is time-consuming to determine precisely where the mRNA transcription start is effected by any particular promoter, it is convenient simply to insert, say, 100 or more preferably 150 base pairs of promoter DNA immediately preceding the FPV gene which is normally promotes, to ensure good working of the promoter. However, it will be appreciated that, given the time to do experiments previously indicated, portions of promoter DNA could be "chewed off" by restriction enzyme treatment to shorten it, thereby eliminating any unnecessary sequences. Such adaptation is considered to be an immaterial variation of the particular embodiments of the invention described herein. Equally, it would be possible to extend the promoter sequence at the downstream end thereof, e.g. to include a few base pairs of its natural FPV gene sequence. This would normally result in expression in vivo of a translational fusion protein if the foreign gene sequence is arranged to be in frame with the natural FPV gene. However, such a protein is not particularly desired and in fact any short sequence of nucleotides could be positioned between the promoter DNA and the start codon of the foreign gene.

The restriction sites. A, B are located in the plasmid DNA flanking the FPV promoter DNA and the foreign gene. Of course, A could be within the promoter DNA if it falls within a non-functional portion thereof. While two different restriction sites have been shown for simplicity they could of course be the same. They can be sticky- or blunt-ended sites and can be prepared artificially by filling in and/or ligating additional nucleotides, in ways well known in the recombinant DNA field. Conveniently A and B in the type 2 construct are converted into identical blunt-ended sites (C, not shown) and then allowed to recombine at a single blunt-ended site C (replacing A, B) within the NER. Care will have to be taken, of course, to select sites which are unique in the vector DNA to prevent recombination of other sequences of DNA from occurring.

DNA from the two plasmids are ligated together in vitro and then transformed into the host, with suitable restriction enzymes. To produce the final construct of type 1. The promoter-foreign gene construction of type 2 is, of course, made in a similar way from a vector containing the promoter and another containing the foreign gene.

FIG. 3 illustrates another method of preparing recombinant vectors of the invention. In this method one first prepares a construct comprising a first part of the NER followed by the FPV promoter of the invention, followed by a short sequence of nucleotides containing at least one cloning site for introduction of a foreign gene, followed by a second part of the NER, which could be simply substantially the remainder of the NER. Of course, virtually any length of DNA would provide a cloning site suitable in some way or other for introducing a foreign gene. Preferably these constructs contain a multiple cloning site, that is to say a short length of DNA containing the sites of a variety of different restriction enzymes, for example at least ten. Such a construct then has versatility, since it will then be much easier to restrict DNA flanking almost any foreign gene at sites close to each end thereof and insert the foreign gene into the multiple cloning site illustrated in FIG. 3. Only two sites X, Y have been shown, for simplicity and, again, these can be filled in and extended or chewed back, as desired, to give identical blunt-ended sites (Z, replacing X, Y). In the final constructs, the promoter DNA will be separated from the foreign gene by a portion of the multiple cloning site, but this will not adversely affect the transcription of the mRNA in the final virus.

In either method of construction, the NER is split by the promoter and foreign gene. It is, of course, not essential that it be split in a central region. Nor is it essential that the second portion of the NER constitutes the entire balance or remainder of the NER. So long as each end of the NER contains or is flanked by a long enough stretch of DNA for homologous recombination, it does not matter that a part of the NER might be excised somewhere in between or that additional (irrelevant) DNA be inserted in preparing the recombination vector. Obviously, it is not necessary that the NER used be the complete region or gene identified in the FPV genome as non-essential. Any part of it will do, and the term "end" in relation to the NER then means the end of the selected part.

References herein to vectors other than FPV (or VV) means any convenient prokaryotic or eukaryotic cloning vector appropriate for bulk production of the construct within a suitable host. Prokaryotic vectors will ordinarily be plasmids or phages. Suitable prokaryotic hosts include bacteria. Eukaryotic vectors such as those of fungi, yeasts and the animal cells, e.g. SV40, can be employed if thought more convenient.

Although the recombination vector used will ordinarily be of double-stranded DNA, it is possible to use single-stranded DNA for the homologous recombination.

The recombination plasmid of the invention containing the NER, promoter and foreign gene then has to be "swapped over" for FPV DNA in a homologous recombination procedure. For this purpose, appropriate poultry cells are infected with FPV. It is best not to use wild type FPV for obvious reasons. FPV can readily be attenuated (mutated to make it less virulent), by any conventional method of attenuation.

Many different methods are available for selecting the recombinant viruses, and have been described for VV in the review article of M. Mackett and G. L. Smith supra. Such methods are applicable in the present invention. Using the TK gene as the NER, one method is to transfer the mixture of viruses containing the desired (recombinant) virus to fresh TK minus cells in a growth medium containing BUdR. BUdR kills the original virus which was TK positive, so that TK minus mutants produced according to the invention can be selected. Another method is to enlarge the recombination plasmid to include a FPV or, less desirably, a VV promoter together with an additional marker gene, preferably selectable such as Ecogpt, but possibly non-selectable such as beta-galactosidase, within the NER and then detect recombinants by using a property of the marker gene, e.g. for beta-galactosidase the blue plaques generated when the 5-bromo-4-chloro-3-inodlyl-D-galactopyranoside (X-gal) substrate is present in the growth medium.

The selected TK minus cells containing the FPV (which has a deleted TK gene but possesses the foreign gene) are then grown in chicken embryo fibroblasts (CEFs), chicken fibroblasts, chick embryo epithelial cells derived by conventional tissue culture methods, principally trypsinisation of tissues or the chorioallantoic membrane (CAM) of embryonated chicken or turkey eggs. For administration to birds, the recombinant a virus can be given to birds by aerosol, drinking water, oral, intramuscular injection or inoculation into the wing web. Ingredients such as skimmed milk or glycerol can be used to stabilise the virus.

While the invention is intended primarily for the treatment of chickens it is potentially of interest in relation to other animals which might safely be infected with FPV. It is even possible that it might be considered safe to infect humans with FPV after appropriate trials have taken place.

The following Examples illustrate the invention.

EXAMPLE 1

MATERIALS AND METHODS

1. Virus strain

The HP438 strain of the fowlpox virus was obtained from Professors A. Mayr and H. Mahnel, Ludwig-Maximillians University, Munich. The HP438 strain has been obtained from the pathogenic HP1 strain by 438 passages in chick embryo fibroblast (CEFs) in tissue culture A. Mayr et al., Zentralblatt für Veterina medizin B13, 1–13 (1966). The HP441 strain used to obtain DNA for cloning was derived by 3 further passages in CEF cells.

2. Tissue culture medium

CEF cells were grown in 199 (Wellcome) medium, supplemented with Penicillin (200U/ml, Streptomycin (200 μg/ml, Fungizone (2 μg/ml) and 10% newborn calf serum (CS).

3. Purification of virus and extraction of DNA therefrom

HP441 fowlpox virus was inoculated on to confluent monolayers of CEF cells at a multiplicity of infection of approximately 1 plaque forming unit (pfu) per cell. Cells were pre-washed in serum-free medium, and the virus inoculum was added to the cells in 1 ml of serum-free medium per 75 cm$^2$ bottle. After 10 minutes incubation at 37° C. to allow the virus to adsorb to the cells, 10 ml of medium containing 2% calf serum (CS) was added. After 5 days, a marked cytophathic effect (CPE) was observed, at which time the supernatant was collected. Cellular debris was removed from the supernatant by centrifuging at 2500 rpm for 10 minutes in a Sorvall GSA rotor. The virus was then pelleted from the supernatant by centrifugation at 14000 rpm for 30 minutes in an Sorvall SS34 rotor. The viral pellet was resuspended in 10 mM Tris pH 9.0 and a further low speed spin performed to remove any remaining cellular material.

To extract the DNA from the virus, an equal volume of lysis buffer (100 mM TRIS-HCl pH 7.8, 2mM EDTA, 54% sucrose, 2% SDS, 200 mM 2-mercaptoethanol) was added to the virus suspension. Proteinase K was then added as a solid to 500 μg/ml. This was incubated at 50° C. for 2 hours and then overnight at 4° C. The solution was then extracted slowly and gently for several hours with phenol/- chloroform/isoamyl alcohol (50:48:2 v/v/v, saturated with 10 mM TRIS-HCl pH 7.5, 1 mM EDTA) and then with ether. 2.5 volumes of absolute ethanol were added to precipitate the viral DNA. Viral DNA was resuspended in 10 mM TRIS-HCl ph 7.5, 1 mM EDTA (TE) or in deionised water.

4. Cloning of viral DNA into plasmid vectors

1 μg of FPV DNA was cut with the restriction enzyme BamHI (BRL) and ligated into BamHI-cut, phosphatase-treated pUC13 plasmid (Pharmaci). Following transformation into *E. coli* strain TG1 using standard methods, D. Hanahan, J. Mol. Biol. 166, 557–580 (1983), colonies containing plasmids with inserted DNA fragments were identified by a white colour on X-gal indicator plates. Colonies, were probed with nick-translated (radio-labelled) FPV DNA and plasmids containing FPV DNA inserts were analyzed by restriction digests of plasmid DNA isolated by the method of D. S. Holmes et al., Anal. Biochem. 114, 193–197 (1981) and also of DNA purified on CsCl gradients. A range of recombinant plasmids containing FPV DNA inserts was obtained, and one of the these, called pMH23, of approximately 11.2 kilobases, was selected for sequencing. EcoRI clones of FPV DNA were made in the same way, except that colonies were not probed with radiolabelled viral DNA but were stored in glycerol cultures as a 'library'.

5. Sequencing of pMH23

To sequence the viral insert of pMH23, random subclones of pMH23 were generated by cloning sonicated fragments of pMH23 into SmaI-cut, phosphatase-treated M13 mp10 (Amersham International PLC). Clones containing viral inserts were identified by colony hybridisation with radiolabelled insert from pMH23. Dideoxy sequencing with [$^{35}$S]dATP was used to determine the complete sequence of the viral insert.

6. Random sequencing of the fowlpox virus genome

Recombinant plasmids containing fowlpox DNA inserts were obtained by a similar method to the above, but starting from virus passed a further three times (HP444). Random sequencing of the viral genome was carried out as in section 5 above. Sonicated fragments of viral DNA were cloned into M13 mp10 and sequenced directly without any identification step.

7. Identification of putative promoter sequences

Sequences to be tested as promoters were identified in two ways;
  a) Sequences upstream (immediately 5' of) open reading frames in the pMH23 sequence were likely to act as promoters in the virus and as such were candidates for testing in a transient assay system.
  b) Sequences upstream of a gene highly homologous to the 4b gene of vaccinia virus were selected by comparing the amino acids encoded by the FPV DNA with those encoded by VV 4b.

The open reading frames (ORFs) in pMH23, and the PF4b gene, were identified as follows.

(a) Open reading frames

The complete sequence of the pMH23 insert (the "11.2 kb BamHI fragment") has been determined and is 11,225 nucleotides in length. This sequence is shown below (X=a nucleotide found to differ when sequencing from different M13 clones of FPV; asterisk = stop codon). Computer analysis of the sequence revealed the presence of several ORFs. If only ORFs of greater than 150 bases in length are considered there are nineteen complete potential genes, predicting polypeptides of between 58 and 418 amino acids. The ORFs numbered 1–12 were considered the major ORFs, either because of their size or because of their codon usage. The start and stop positions of these ORFs are shown in Table 1 below. Seven other ORFs were considered minor, either because they overlap or are contained within other potential genes, of because of their codon usage.

```
   1 GGATCCGACGCGGCTGCCAAGACCTTTATACCCGACTCTTGTTCTACTGGACGAACGCGG

61 AGATTTAAAGCCATGGCTGACGTATAGTCGAGGACGCCCTCGGTAATAAATTGATTATAT

121 TTTCAGTTTTAAAAAATTAATTTATATGTACTCAATATCCTTATATAGAATTATTTTATC

181 TCTTCTGATATACGTTAGGTAGATGCCGTTCAAATAATAAAATATCTGATGACGTTTTTA

241 TGCGCGTGTTACGTTATTATAATAGATAATAGAAATAAACGTTAAAATAATAATTAATTA

301 TCTTTTCAGTTGTTAAATATATTCTAGTTTTATAAGCGTTATTCATATATAAAAAATATA

361 AAAACTAAATCGTATTTATTATGATGCTACGGCGGTCATTTAACAAATTTACGCGATGGA

421 GTTCGGTTGTACGGGAACTAATAACCAGTTGGCCGTTCACAGATTTACAGAAACGCGTTT

481 TACATCTTTCAAAAAAGAACTTTTAGTTAATTTAGGAATAAGTGACTTAAATGATATAAA

541 AAACATATGCGAGGATTCTAAAATATTCTTTCCGGAAAAGAGAACGGAGCTCTTAAGTAT

601 TAAAGATCGTAAATCTAAACAAATAGTTTTCGAAAACTCCCTAAACGATGACTTGCTTAA

661 AAAATTACACGCCTTGATCTATGATGAATTAAGTACGGTAGTAGATTCCGTTACCGTAGA

721 GAATACCGTTACATTGATTATGTATGAAAAAGGAGATTACTTTGCCAGGCATAGAGATTT

781 TAGTACCGTCTTTTCTAAAAACATAATATGCGTTCACCTGCTTCTATATTTGGAACAACC

841 AGAAACGGGAGGTGAAACGGTTATATATATCGATAATAATACGTCAGTGAAATTAAAAAC

901 AGATCATCTATTTGATAAAACTATAGAACATGAAAGTATTACCGTTGAAAGCGGTAGAAA

961 ATGCGTGGCGTTATTCGATGTCTTACTAGAAAAAAAGTTATCCGCGTCAACAAACGTAAT

1021 AGGTAGCATAGAATACTTAGGTAAAAAAATAAATTTATATGACAGAGAAAATGATCTTCA

1081 GTTGTGTTATTGTGATATGGTAATAGAAAGAATGACAGAAGATAAAGAATATAGCCTAGG

1141 AATGATATCTGATAGATCAGGTAGATGTATAAAATCTCATCATAACGGTAGTATTGTTAG
```

```
1201 ATACCGTAAAGAAGAATATGGATCTTTCGATGCTCTATGTATATATAACATGAATGAAGT
1261 GGATGAAATTTGGACTGGTGATAAGAAACATATTATATGGTCTACTATTGATAAAAAAAC
1321 AGGAACGTCTTTTATACCTATAGATCCTGTACTTTACGAAAAGTTAAAAGCTATTTCTTC
1381 TAAAGAGCATAAAGAATACAAAGATTTGAGAGGGTTTTGTAATAGCAGAACGGAGTATAT
1441 TTGTTGTTCGGTATCTAAGTACTATTTCGACTTACCTA- CAAAAACAGATTTAATACACGA
1501 GGTGATTAATTCTATCGATTATGATACTAAGTCAGTGGGTACACCCGAGTGGTATACTCT
1561 GCCTATACAAGTTAAACAAACTATCCTAGGTAATATGTCTTACGAAGAGTTATTTAATAT
1621 AGTAAGAGGTAATATAGCTCTTGAAGAAGACAATGAATATGGCTGTGATTAACATTAATG
1681 GTAATACTTTTCTAAAAACTAATCTCAAGTATTGTTTACAAGCGACTGAAGTAATAGTTT
1741 TAGCAAAATAATACCTTTACTGTTAGTTCTACAATCGAAATTATGCTGTAACATGAGGTA
1801 AGGATATATTTATTAATACGTTACATCTTTCGAAAGACTTTGATCGTAGTATAATATTAT
1861 ACATCTGCTCTACTTATTATACATAAGAAAATTTGTATTTTATTTAGTGCGCTGATAAAT
1921 CGTGTTTAAAGTATACAACGGACGTCTATTTCCAAAAAATCTGCGCGTGTTAACGGATTA
1981 AAATCTACATGAAAATATCTCTTAAACTTTATTTCTACGTATAACAAACAACAGACTGAT
2041 TTTATATATTACGAATAACTATTTTCTTAGGTTTTTTATATAGATGCTATACAGTGTTTT
2101 TACGCGTATATACAAAATACGGAAAAATAATAXAACAGAAATGATTCTGGCAATATACGA
2161 CCGCAATGCCTATATTGTTAAAAAAACAGGTATCGGAAGTATCTTGTTACGCGATAACGG
2221 TACTAGGAATACTATGCTTAATATTATTTACGATACTAGTAGTCGTAACATGCAAATGGT
2281 ATTACGCGTTTCCGTACTTTAGCAAGGTATGTCCTGATGAGTGGATAGGATATAATAGTA
2341 AATGCTACTACTTTACTATCAATGAAACTAATTGGAATGATAGCAAAAAACTATGCGATG
2401 TTATGGATTCTTCATTGATAAGGTTCGATAACATAGAAACTCTAAATTTCGTGTCGCGAT
2461 ACGGTAAGGGTAGTTACTGGATAGACATAAATCAAAATAGAAAAATTCCGGGTATTAATT
2521 TCTCACTATATTATGAACAAGGCGTTAATGATATTTGTCTATTATTTGACACGAGTAACA
2581 TTATCGAAATGTCTTGTATATTTCACGAAAGAACGATATGTGTTAAAGAAGATAGATACA
2641 CCCATTGGTATACCGAATACATGCGTTAGATTTACTACCTCTTTTTTATACAATAGTATT
2701 TTGTACGTTCTTGTAAACAGAAAATCCGTATAGTTTATATTTTTAATCAAAGTAATAACG
2761 AATATCTCGATGTCACGTATAAACGCAGATTCTAGATATTAAATTCTCAACGTACGTCAT
2821 TTGCATTCCCTGAGATGATACTTTGCTATTTTATTATACCGTAGTCTATACAACCACTAC
2881 AAAGTTAAACGAAGTAAAATTATTGATTCGTTGTTATTATTTCAGCACAGTAGTACTCGC
2941 TATCTTCGTTTAAATCTAATAACACGCCCTTTGAAACATTTTTGTGCTAGATAATAATAC
3001 GTTATTATTACACTAACCTGTATTTCTTCTAATCTTTAAGGTGTGCTAACGATATATCAC
3061 GGGATTAAAAGGTTATTAGTAGTCGTATAACAACATAATAATAGCACATCTGTATATTTA
3121 TATACCTCTCGAGTACATAAAAATAATATGTTTTGATAAAACGTAAATCAATAAGTGTAT
3181 AAGGTATTATTTCTTTTAATGAAGAAATAGGACGTAATGTCTAAATCAGATTTATATTCC
3241 CGAAAATATTTTTCTTAGATGTATATGTTAGTTAAATTACGTGATTATATTATAAGTTAT
3301 CTGCTTACTTTAACATTATATAGTAATTATATACTAACCGATCTTAACACTTCCGTACAA
3361 AGAGGTATGCCCGCATCTGCGAGATATTGTGATTTTCGTATTTAGATATGTGAATATAGT
3421 TATCTACTAACGCGACTTTCCTCCAATTTACAAAGCTCTAAGGAAAAAAAATAAAATAAT
3481 ACTACCACGTTCCTCTTTTAAGAGTTAACTATTTACTCGGAGGTATCGGTATACATACAA
3541 TTCTATATAATTTAGTTAATCGCTTTTTACGCGCATAAGTCTACGTATAATGTCTTTGTT
3601 TAAGTAACTATCCCTGGAATATTCCTAAAAATAGCGGAATTTTTGTTTGTACGTCGGCTA
3661 CTAGGAACATGAAAGGTACGTTCGCTTTTACGATAGGAATTTTCTTTATTCCGTCTGTAG
```

-continued

```
3721 TGCATAATTCGGTAACACTAGCTGCTTCAGTTCCGTATTCATCTACTTTTATCACAGATT
3781 TTTGCCTGATATTACCTATCCTCAAAGTTTTTGTATCGGATATACCTACTAATTCACCTG
3841 ACTTGAATAGATCATTACATCCCATATGGATTAGCGCGTCTTTCAAGTCTACGTCATCTT
3901 CTAATTCGAATTTAGGTAAATAAAGAACTATTTCTTTCAAAGTCATATCTTTTTTAGATA
3961 TTATTTTATTGATATTCTTACCGTTATTGAGAGAATCAACTACTCCTAAAATAGAAAAAG
4021 TATTAAAATTACGTAAACATATTAGTTTTAACATCTTTTTATTTGTTTAGTATATAAACT
4081 TATATCGTAAAGAAATATAGTTCTCTTAATTTACGTTTATTAGGAAATAAAATAGACATA
4141 TAGATATACACCTTAGATACTTAATTAAAATGGATAGAAACATTAATTTACCCGAAGAAG
4201 AGCTTAAATATATAAAAGAATGTTGCGAAGTTCTTTATTTACCCCAGCCGACGAGAATGG
4261 ATATAATCGGTGTTATGAATGATAGCGATATTTCTTGGAATGAAAATCTCATCATTCTAA
4321 TGTCGGAAGATGGTAAGATTTATGTGTACGACGATGAAGCTCTATACAAAGTAGCGGATA
4381 CTATGGAAGAGTTCTCTGAAATAGGACTTATTAATCTA GGAAATGAAGTTTATCATTGTA
4441 GAGAGGATATAAAACCTCTTCCCGAAGAGGATAGGGATAAGGATGAGTATATAATGAAGA
4501 TAAGGGAAAAAGCCAGGCAGCTTATAGATAATTCACAAAAAGATTTTGAGGCCATTCTAG
4561 ATTCTTTGGAGAATAAACATGTATCAATTTAGGTATATAATATAAGGTAGCAAAATACGT
4621 ATGTCCGTGTACGCTTATGTATTTTTTTATTTGGATTAAAATCGATACGCTAGAGAATAG
4681 CGGAGTAGCTTCTGTATCCGCCGCGGTTATTTACTTTAGTAATCTATTAAACTACTTTTA
4741 TCTCTATTATTAAGTTAGTCATACCCACGAATATATATTCATAAAAACATCTTCCTCTCA
```

```
                 *  K  L  K  T  L  E  E  K  L  C  K  N
4801 GATTTTCATCCGTAAAATTATTACTTTAATTTTGTTAACTCTTCTTTTAAACATTTATTT
      E  E  K  L  A  L  L  Q  I  R  I  E  T  I  Y  R  S  Y  I  N
4861 TCCTCTTTGAGAGCTAAAAGTTGTATTCTAATTTCGGTTATATACCTACTATAAATATTA
      D  I  I  K  Y  Q  N  K  L  Q  D  V  I  M  C  L  E  K  I  E
4921 TCTATAATTTTATATTGGTTCTTAAGTTGATCTACTATCATACATAATTCTTTTATCTCT
      Q  R  Y  K  E  D  L  E  K  L  I  S  N  C  K  I  D  I  E  S
4981 TGGCGATATTTTTCTCGAGTTCTTTTAGAATACTATTACACTTTATATCAATTTCTGAT
      K  I  E  K  I  N  S  D  Y  E  E  N  I  T  K  I  F  D  S  M
5041 TTTATTTCTTTTATGTTACTATCATATTCTTCATTTATTGTTTTTATGAAATCACTCATT
                                                        (ORF5)
      V  S  G  L  A  K  N  N  R  R  I  I  M
5101 ACACTTCCAAGAGCTTTATTATTCCTACGTATTATCATTTTAAAAATCTAAATTATTGTT
5161 TATTATATTTACATATGTTATAAACATTATTTTTAAGTATTGCCAATTAATAAATATAGT
5221 TCATCACGATCATCTGAAGTATCTTATCATCCCGCGGCATAATTTTATATTTTAGTATAT
5281 TTGGTTTATTACGTGCGTAGATTTAGAATCTTTATTCACACCCGATTATTGTGTTGATAG
5341 TATATAATATTAAAACAATGGAGTTTTAAGCTCTACCAGAAGATATCATTAAGTATAGCG
5401 TTCTATATGATCTAAAACATGTATATTGTACCTAGTGATAATAGCATTTTTACCATTTTC
5461 GTTTATATTGCTAGCTCATCTATACGTAACTTTATGGTTTATTAGCTATCTCATGTAACT
5521 ACATATTGTTATCATCGTTTAACAGTATTATTTCTTTTAACTGATCCATTAAACTTTTTT
5581 TATGTATTAGCTCATATTCTAATTGATAAGAATCTTGTATGTAACTATTTATAAACTTTA
5641 CTACCTTCAAAGAAAATAGAGGAGAAATCCAATGTGAAATATGTAATATAAGGTCGCGGT
5701 GGACGTACAATTCACTTGTTTCGCTGTCCGATACCACATTTAATACTATTCCCCTATAAT
5761 CGTAGTAGTCATTGCATGATCTATTTATCCTGTCTAATTCATTTATTAATTCTACGGAGG
5821 ACTCCTTACTCATCCAATCTAATATATCTCTTCCTCTAGAACTACATAACCTTGTAGCAT
5881 TTATGTATTCATTTTCTTTCATCATAATAATTTCTATATCTTCGTAACTTAGCTTACAAA
5941 AGTTATTATTGATCGATTCTACTTTGATTTCCATATTGAATAATTGTTATAAGCTGGAAT
```

6001 ACAAATACTTAATTTTCATAATTTGTTAATAACCTAAATATTTGTATTTCTCTATAAAAA

6061 CCACATACAAAAACTATTTACATTATTATTCCAGACAATAGATTATGGTATTTTTGGGAT

6121 CGGTACAAGCAAGTGTTATAAAGCAAGTAAATCTGGCCTC<u>GAATTC</u>AACATAATCACCTT

6181 CCACAACATAACCGCTTTCTTCTTCCGAAGATTCGGACAATCGCTATGATAAAAGTATTT

6241 ACTAGTCGTTGAAATAAAGATGTAGAATTGCCCATTATATTATAATTTAGTCACTTATTT

6301 GTTTATTTTTTTAGTACACGCTCTATCTTTCTTTACATCATAAGGCAATATTTATCATAT

6361 ATCACGATAATCAGGATATTTATATATGTTTAATAACGGCTTTTACGTTTTATTGATTAA

6421 GACGACACGGTAACAAAATTAATATACTTATATTGTACTACATAGTTAGCAAAATATCTA

6481 TTAGAATACTTGTTTTGCCTATGTTTACTTCTATATTGCTATATAAGACTTATCACCTTC

6541 AATATTTCTGTTTGTACCATATTCATGACTAGATTTTTCTATATCAAAATATATATTTAG

6601 TTATAAAAATAATTTTATTTCATAGATGTGATGTCAAGCTCTTTATTGCCTATATATTCA

6661 AGTATGTTGTATTTTATTTCATAGATGCGATGTCAAGCTCTTTATTGCCTATATATTCAA

6721 GTATGTTGTATTTTATTTCGTGGGGTAACCAATTCCATTTTGTTTCATCACCAGTAATTT

6781 TTTCATCTATAACTCGCATCGCTGATTCAATAGCTTCCGCTCTTTGCGATGCCGTGTCTG

6841 CCAATTCTTTTAATAGATATTTGTAGAATATGGCATTATCATACAGACCTAATATTTTTC

6901 TAGAATGTCTTGCCAATATGTTCTCATCAAGATTTTTGGATGGTTTTAAACACAGGTCCA

6961 GAATGTTGTAGGTTCTGATGCTTTCGCTGTTTATTCTCCTTAATTCAATTTTACATTTTT

7021 CAAATACATCTTTTAAACGACTTTTGCTGTTAATGACTGTCATGTTTCTGGAAAATCCTT

7081 TATCCGATGATATTGTATTTGTATATTGTCTTAATGCTATGTCCGCTATCAGCATATCCA

7141 CGGATTCAGATTCTGGATTTGTATCCATATTACAGATCATCTCTAAAGTTGTGTGTTCTT

7201 CATTCATCACGGTAAACACAATGTTACTATCAGCGCCTCTCTTGAGAAACATGCTTACCA

7261 TATCTATTTTGTTGTTTTGTATAGCGTAGCACATCGCTGTCACACAGGGCCTTTTGCTGA

7321 AATAGTCAATGTTTGCTCCGGAATCTAGCAACATCCTGCATACTTCTGTGTCTCCTTTGC

7381 TCATGGCGATGATAAGGGGAGTACATCCGTAGCAATCTTCTATGTTGGTACAGGCTCTGT

7441 GATCTAATAGCAATTCTATACCTTTAATATCTTTTGACATAACAGCTAAATGGAGAGGCG

7501 TAAAACGATCAGTGTTGGGCACATCAGTGTCGGCTCCTCTAGCTATAAGGAGCCTCATCA

7561 TGTCAAGATTTTTACTAATTGTGGCCAAATGTAAGGGAGTGTTTCCTTTCTTGTAGATAA

7621 CATCATTTATGAACTTTCCAGAATCTAATAATTCTTCCACTTTAACAACGTCTCCTTCTT

7681 CCACGGCCTCATGCAATTCAGATTCTATATCCGGATAGTTATAATCGGGATAAGTGTTGT

7741 AACTCATCAGTAATTTAATCATTTCAACATCTCTAAGTCTGACGGCCATCTTTATAGGCG

7801 AGTATCCGTTGATAGTAAAATTCGGATTGATGTAAGAATCCAACAGGCGTCTAGCCACAT

7861 CCAGTTCTCCAAAGAGAATAGCATTGCAAAGTTCTACACGATCCATTGTATAATATAGGT

7921 GTTCAACACCTCTCGATATATCATTATTTGTTTTTTCAATTTTATTATAAGTAGTTTGAA
                          (ORF8)

M E E G K
7981 TGCATTTTTAAGTTTAATAAATCTTGATAAAGTATATTTAAAAAATGGAGGAGGGTAAAC

P R R S S A V L W M L I P C G S I I I V
8041 CGCGACGTAGTAGCGCAGTATTATGGATGTTGATTCCATGCGGAAGTATTATTATCGTGC

L S V F V I I L S T R P P V P P D I K I
8101 TATCTGTATTTGTGATTATTTTATCCACAAGACCTCCTGTACCTCCAGATATTAAAATAC

L Y C K E G W V G Y N K N C Y F F S E E
8161 TTTACTGTAAAGAAGGATGGGTAGGATATAATAAAAACTGCTATTTTTTCTCTGAGGAAA

K N N K S L A V E R C K K M D G H L T S
8221 AAAATAATAAATCATTAGCTGTAGAAAGATGTAAGGATATGGACGGGCATCTGACTTCAA

```
           I   S   S   K   E   E   F   K   F   I   L   R   Y   K   G   P   G   N   H   W
8281 TTTCTAGCAAAGAAGAATTTAAATTTATCCTAAGATACAAAGGTCCGGGAAATCACTGGA

I   G   I   E   K   V   D   F   N   G   T   *
8341 TTGGAATAGAAAAAGTTGATTTTAATGGAACTTAGAAATTAGAAGATGGGTCATCTTATG

8401 ATAATATAGTTCCTATCAAAGGAATAGGTGATTGTGCATATTTAAGCGATAGATCTATAA

8461 TGTCGTCATTTTGTTTTTTACCGAAGAAGTGGATATGCAGAATAATACTTTTATAGAAAT

8521 GCTAGCTAATAATGTATAATATTTTTATGAAAAAATGGAAATTGATATGCATAATTATAA

8581 CCAAAAGTATGATATTGCAAGATGTCTTGTATACTTTGATCATAGGTATACATGAGCAGT

8641 TTAAAATATGCAAATACAGATATAACTATTAAGATGGTGATAATAACACCGAAAGTCTTG

8701 GAAGATGATAGTTTATCAGAATCAAGTATCCATTTTGCGAATAACAGATTCCATTTTGAT

8761 TTGTATTATATAAAGCCTTGGGCCTTCGTAAGTATATTATATTTATTTTTATGTTTTTTA

*   E   Y   N   N   A   V   A   P   K   A   T
8821 TATAATATTATTTAAAACCTTTACTATTCGTAATTATTCGCTACCGCTGGTTTTGCCGTT

T   E   I   Y   D   R   I   K   V   I   I   E   N   F   S   D   G   S   L   M
8881 GTTTCTATATAGTCTCTTATTTTTACTATTATTTCATTAAATGAATCACCACTAAGCATA

I   K   S   I   N   I   R   D   E   A   H   Q   K   R   I   G   S   I   I   S
8941 ATTTTAGATATATTAATACGATCTTCTGCGTGTTGTTTTCTTATGCCGCTAATTATTGAC

L   Y   R   R   N   N   E   E   I   E   A   E   I   A   A   I   M   E   D   T
9001 AAATAGCGACGATTATTTTCTTCAATTTCAGCTTCTATAGCAGCTATCATTTCATCTGTA

R   I   D   E   N   N   D   I   D   Q   E   M   S   Y   D   K   E   L   V   R
9061 CGGATATCTTCGTTATTATCTATATCCTGTTCCATAGAATAGTCTTTTTCTAATACTCTT

E   A   K   T   L   L   Y   T   S   L   K   S   Y   Y   S   T   E   I   E   K
9121 TCAGCTTTTGTTAGTAAATAAGTACTCAATTTACTGTAATAAGATGTTTCTATTTCTTTA

F   R   N   S   I   D   K   I   S   R   D   Y   V   E   D   I   K   S   I   Q
9181 AAGCGATTACTTATATCCTTTATAGATCTATCATAAACTTCGTCTATTTTGGAAATCTGA

N   Q   L   E   Q   S   H   D   I   D   K   E   T   E   I   N   L   A   V   C
9241 TTCTGTAGTTCTTGGCTATGGTCTATATCTTTTTCAGTTTCTATGTTTAGCGCTACGCAT

R   R   Y   Y   R   M   L   I   S   V   R   T   A   V   Y   P   S   I   W   P
9301 CGTCTATAGTATCTCATGAGAATAGATACTCTAGTCGCTACATATGGAGAAATCCATGGA

I   V   Y   D   L   L   L   Q   S   V   Y   E   G   N   I   K   I   R   T   H
9361 ATTACATAGTCCAGTAGTAATTGTGAAACGTATTCTCCGTTTATTTTTATTCTAGTATGC

R   I   N   I   I   P   D   H   L   K   N   N   D   K   L   T   N   L   L   R
9421 CTAATATTTATTATCGGATCGTGTAACTTGTTGTTATCTTTTAATGTATTGAGCAATCTC

R   S   S   E   L   Q   K   W   D   N   F   D   K   G   E   L   N   C   L   R
9481 CTAGACGATTCTAATTGCTTCCAATCATTAAAATCTTTGCCTTCTAAGTTGCATAATCTA

T   I   N   V   F   G   N   S   R   M   I   V   V   E   V   D   L   L   K   M
9541 GTAATATTTACGAACCCGTTACTTCTCATAATTACTACTTCTACATCTAATAATTTCATA

S   M   F   Y   E   N   I   G   C   I   K   I   D   I   I   N   M   K   K   I
9601 GACATAAAATACTCATTAATGCCGCATATTTTTATATCTGTTATATTCATCTTCTTGATA
        (ORF10)

T   N   R   V   E   K   F   K   M
9661 GTATTTCTAACTTCCTTAAATTTCATTATTATTTAGTATACTCTACAAAGTAACTAAATA

9721 AGTTTATTTTATTTATCGGTTTTATACAAATATAAAATTTTTCTATGGTGCATATATCAC

9781 ATCCTACTATATTACTATATAAGAAATTACACATATTAATATTTGTACAATCTAGTTCGT

9841 CTACTATTTTTATCCAATAGTCCTTAGATGTATTTAATAAGCCACTATTCGTATTTATGT

9901 TAATATTATTCCCACCGCCAAGATTATCACATACCATCATGCTATCATCCCAACTTAACT

9961 TATTTTCGGAAATAAAATAACATAAATTATCGAATTCTAACCAGTCTTTACCACACCTTA

10021 CTAAATATCTATCTCTGTCTATATCTACTAAAATAATAACAAATAACAATATAGTGAAAG

10081 CTATCGTTAATAGACCGCGTTTCCTAGCTTTTTTACACATTTTCTTATCATATTTATATT

10141 ACTGTTTTTTACAATTTTTAATATTATTTGTCTCATTTTGTAGTAGTAGATTTCGTAAGA
```

```
10201 TCATGTCATCTAATTTTGTCAGTATCATCCATCTAATTTCTATGGGTAAAGTATACCATT
10261 TTGTATTTACTAGGTTTGCATTCATTATATTGTTTATCTCTAATAACATTTCATATCTTT
10321 TTGTCAACATTTTTAATATATTTTGTATTATACGAAAACAGTTGGGAAATATTGTTTTGA
10381 TTATATTCATTTTTTCTAATAATGTATCGGACAGTCTATACACTATAGCGATGTTATCTT
10441 CGTTAGATAATAAATCGAAAAGACTTAAATCTTGAAAAGAATTTCCGTCGTATATCTTGA
10501 ACGTTTTCATACGTTCTATTTCTTCTTTTATAATATTTATGCAGGAACTTAAGTATTCAC
10561 ACTTATTAATTATTTTCATATTCTTTTCCATTCCGTTAGAAATTCTAGCTTTGTAAGATA
10621 AGTAATACAATGATACTATATAGTTAGCAAGAATAATAGCATTATTGTTAATAGTATGTA
10681 ACATAAAGGTGTATTCCCTCATCATCTAAAGCGTTATATCAGCACCGTGGTCTATTAATA
10741 CCAATATATTACTAAAATCATTATATCGTTCTAATATTATTCGTGTAATATATTCTACCC
10801 ATTCTTCCTTTATATTTATATTAGCTCCTCTAGATATGATGTAATCTAATAGGTCGTCGG
10861 TAATAAACCTAGTTTCGTATAAGGGGGATGTATTAGTTAAAACGCTTTGTTTGTTAATAT
10921 CGGCGCCGTGGTCTAATAATACTTTTATTATTTTTAATCTAAACGGATCGTATACTTTCA
10981 TAGCGTAATGTATAGGGTATTTACCATTCGCGCCGTCTTCTGAATTAATGTCAGCGCCGT
11041 ATTCTATAAGCAATTTTACTATTTTACTTTCTGTTCTATTAGCAGCTATATGTATAGGTT
11101 TCAAACAATAATGTTCTAAATTAACAATAGCTCCGTATTCTAATAGCGATCTAGCTATAT
11161 CTACACAACCTTTTTTTATAGCCTTATGTAATGGTGGTGTAAAGAACCCAGAAATGTTAG
11221 GATCC
```

TABLE 1

Open reading frames in the fowlpox BamHI fragment in pMH23.

| ORF | Start | Stop | No. of amino acids | Size in kilodaltons |
|---|---|---|---|---|
| 1 | 416 | 1672 | 418 | 48.2 |
| 2 | 2166 | 2669 | 167 | 19.8 |
| 3 | 4054 | 3608* | 148 | 16.4 |
| 4 | 4170 | 4592 | 140 | 16.5 |
| 5 | 5138 | 4821* | 105 | 12.5 |
| 6 | 5974 | 5519* | 151 | 17.9 |
| 7 | 7906 | 6674* | 410 | 46.8 |
| 8 | 8025 | 8374 | 116 | 13.2 |
| 9 | 8632 | 8835 | 67 | 7.9 |
| 10 | 9686 | 8844* | 280 | 33.0 |
| 11 | 10120 | 9689* | 143 | 16.6 |
| 12 | 10705 | 10139* | 188 | 22.4 |

*ORFs 3, 5, 6, 7, 10, 11 and 12 are transcribed on the complementary strand to that shown above, i.e. in the reverse direction to the others.

Sequences upstream of the eleven largest major ORFs were cloned into lacZ translational fusion vectors for the measurement of promoter activity in a transient assay system.

(b) FP4b gene

Random clones of fowlpox virus DNA were sequenced. The sequence of each clone was translated on the computer into the six possible frames and compared to a library of published vaccinia sequences. Several fowlpox genes with some degree of homology to vaccinia genes were detected. One gene identified in this way was a fowlpox gene highly homologous to the vaccinia 4b gene (this is referred to herein as the FP4b gene). The M13 clone containing these sequences was used to probe an EcoRI library of fowlpox virus clones (see above) and a clone containing DNA of 2.7 kilobases was detected. The clone was sequenced as described for pMH23 and found to contain the 5' end of the FP4b gene, upstream putative promoter sequences, and the 3' end of another open reading frame.

8. Assay for strength of promoter (a) Translational fusion vectors.

Translational fusion vectors allow potential promoter sequences, up to and including the initiation codon of the test gene, to be fused to a gene with an easily assayable product. Thus the promoter sequences under test are in exactly the same sequence context relative to the start of the ORF as in the original gene, and only the coding sequences of the gene are altered. The translational fusion vectors used in this case have the beta-galactosidase gene (lacZ) as an assayable marker and are called ppNM480, pNM481 and pNM482. They are modifications of pMC1403, J. J. Casadaban et al., J. Bacteriology 143, 971–980 (1980) made by Minton, Gene 31, 269–273 (1984). The modified vectors have additional unique cloning sites available in all three reading frames.

(b) Cloning fowlpox sequences into translational fusion vectors.

Figure 2:
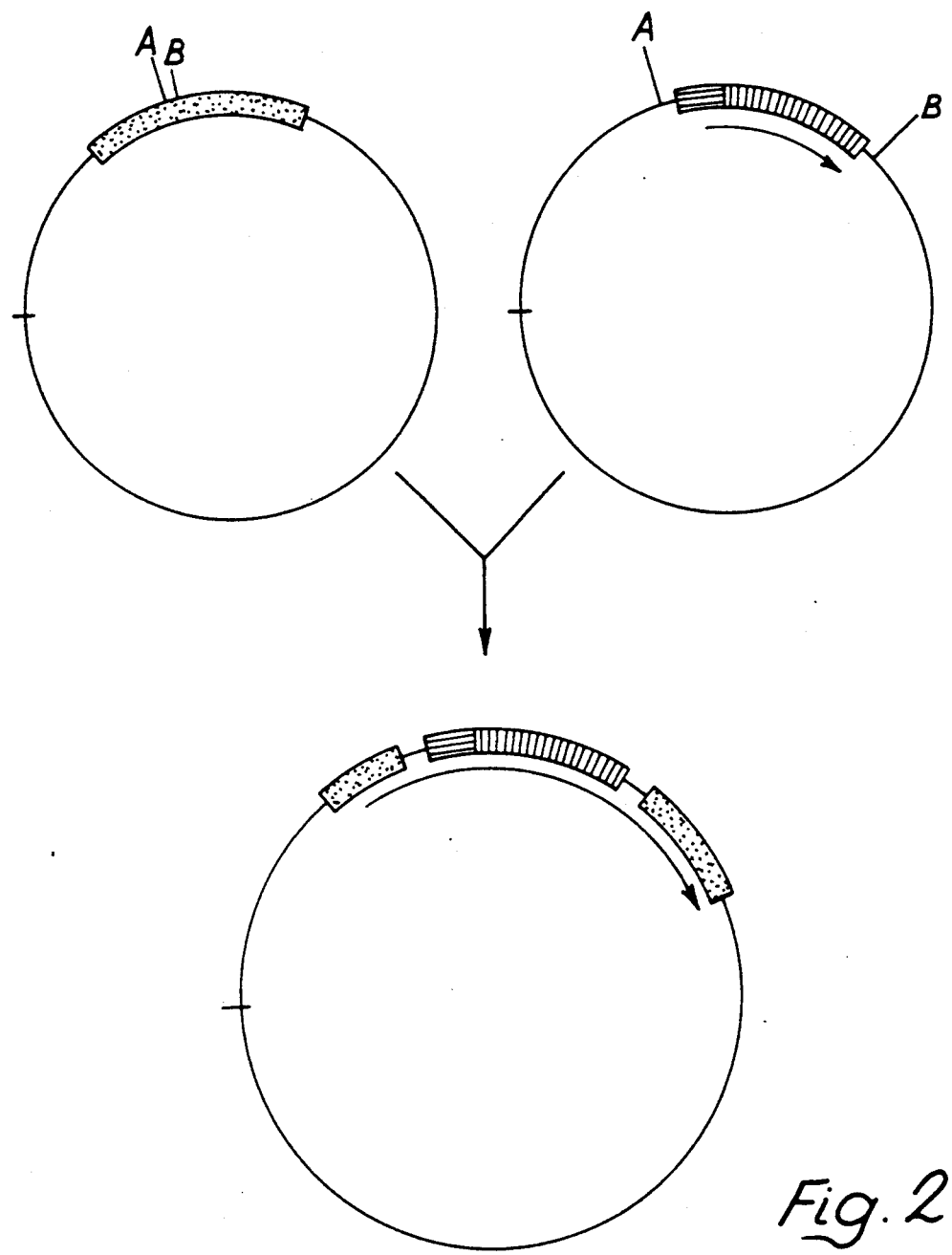
FIG. 2 and 3 are plasmid maps showing schematically the derivation of recombination vectors of the invention useful in the homologous recombination.
Figure 3:
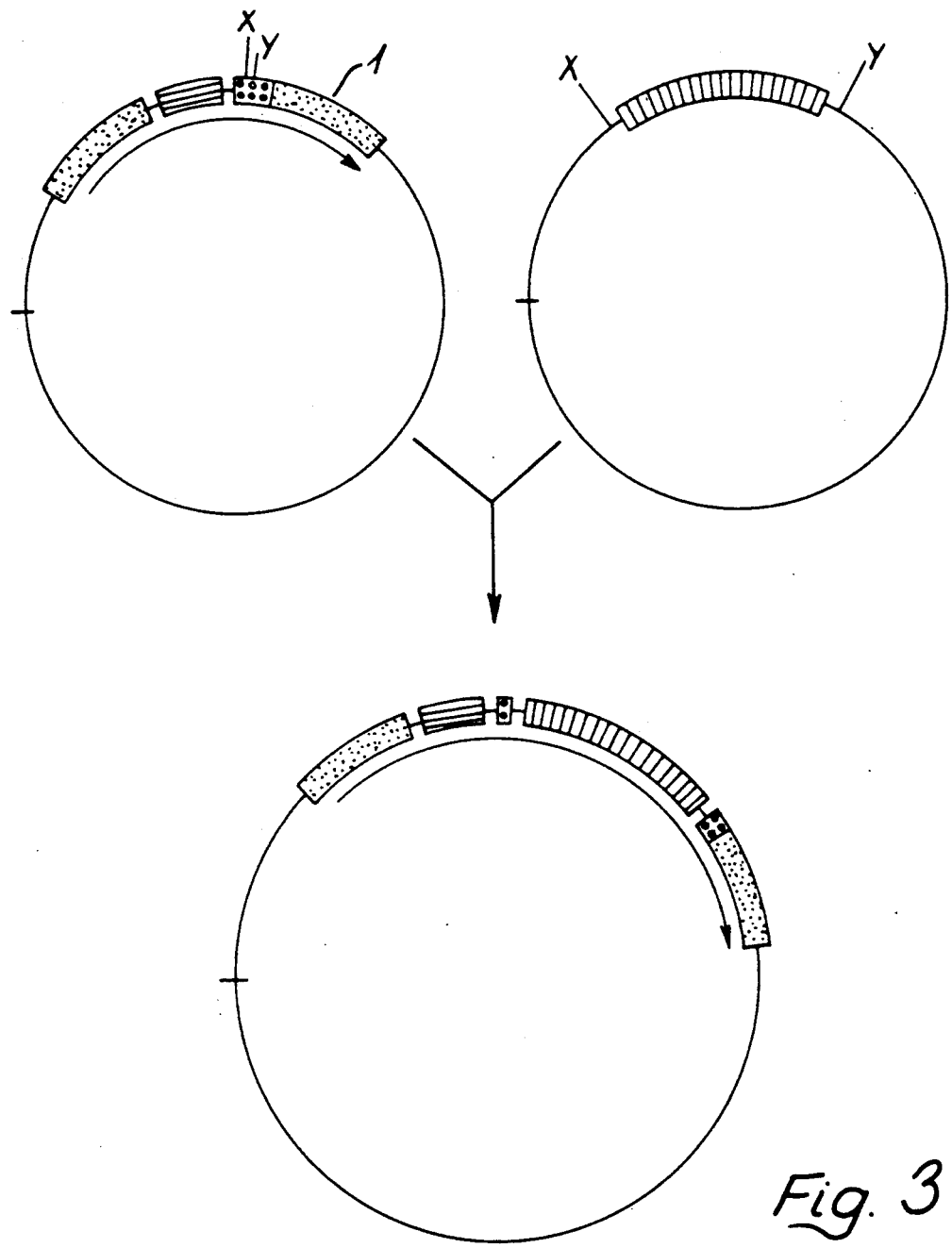
Figure 4:
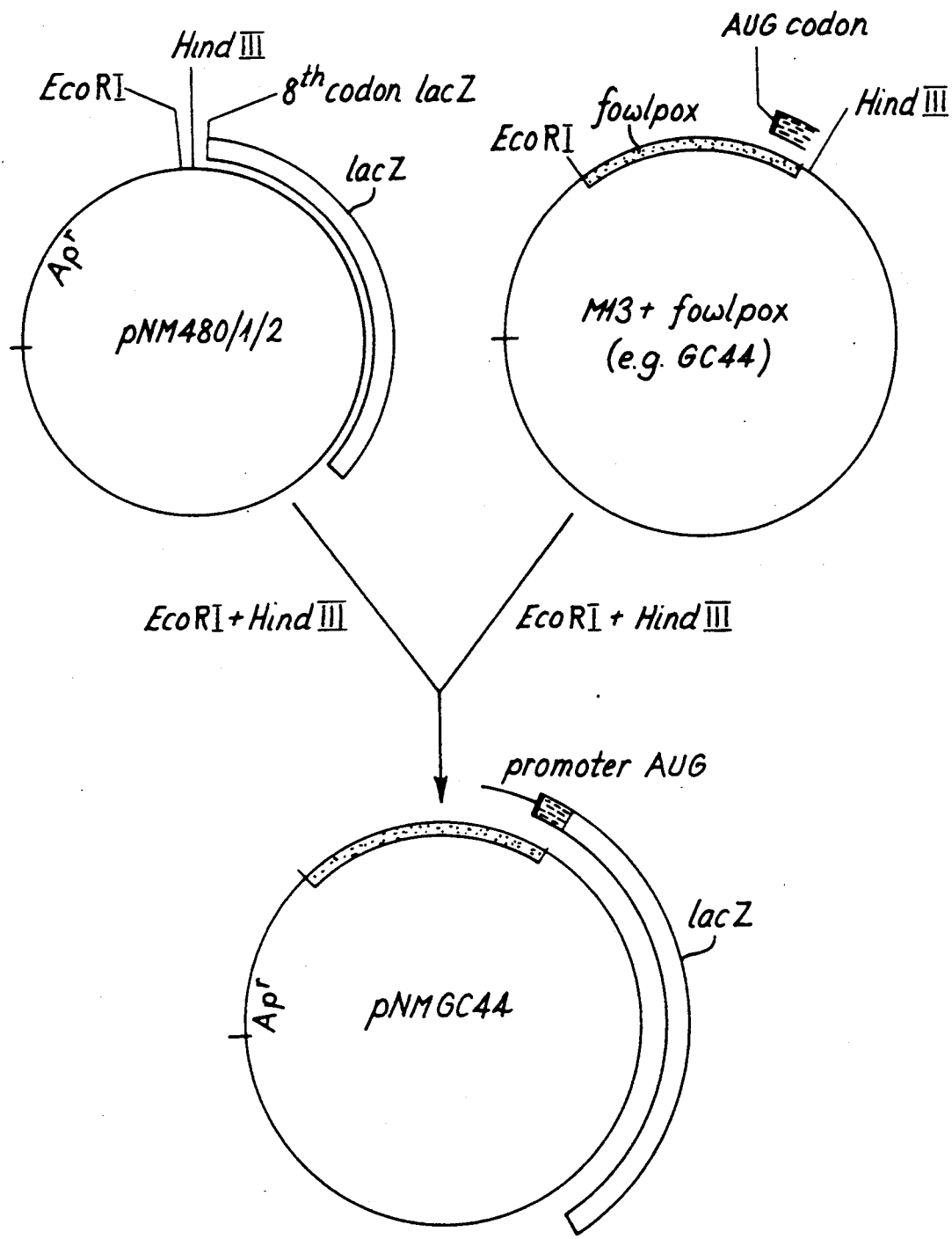
FIG. 4 is a plasmid map showing the derivation of a construct for testing FPV promoters of the invention in a transient assay.

Random M13 subclones generated for sequencing purposes were used to place test sequences upstream of the lacZ gene. M13 clones which started just downstream of an ATG codon and ran in an upstream direction (into the putative promoter) were selected. Fragments were excised from the clones, using restriction enzymes sites in the M13 polylinker, and cloned into pNM vectors cut with suitable restriction enzymes. The appropriate clone was chosen so that relatively little of the FPV gene ORF was present in the fused protein, and the appropriate vector was chosen so that the few amino acids encoded by the FPV ORF were in frame with the lacZ gene. For that reason the vectors differed by one or two nucleotides and are designated pNM 480, 481 and 482. Plasmids containing fowlpox sequences which had generated a complete acZ gene were identified tentatively either by a blue colour on bacterial plates or by probing with radiolabelled fowlpox DNA, and definitively by sequencing across the fusion site and into the putative promoter. FIG. 2 shows how all of these clones (except number 1) were cloned into the pNM vectors. (because the only suitable M13 clone for ORF1 was in a different orientation, different restriction enzymes had to be used. The pNM 480 plasmid was cut by BamHI and HindIII, using a BamHI site between the EcoRI and HindIII sites marked, and the HindIII site was end-repeated appropriately to accommodate the BamHI - HaeIII promoter fragment excised from the M13 vector). Table 2 gives a list of the ORFs involved, the name of the M13 clone used, the pNM vector used and the number of amino acids encoded by the fowlpox ORFs (i.e. from the starting methionine codon onwards) participating in the fused products.

TABLE 2

Translational fusion contructs of promoters (plus part of the ORF) with the lacZ gene construct.

| ORF ref. | Starting pNM vector ref. | Final construct vector ref. | No. amino acids of ORF | Nucleotide length of 5'-non-coding sequence |
|---|---|---|---|---|
| 1 | pNM 480 | pNMGF32 | 20 | |
| 2 | pNM 481 | pNMGJ13M | 7 | |
| 3 | pNM 481 | pNMGE23 | 3 | |
| 4 | pNM 482 | pNMGA5 | 13 | |
| 5 | pNM 482 | pNMGK4 | 10 | 189 |
| 6 | pNM 480 | pNMGF6 | 9 | |
| 7 | pNM 482 | pNMGB86 | 13 | |
| 7 | pNM 480 | pNMSAU4 | 2 | |
| 8 | pNM 482 | pNMGC44 | 14 | 395 |
| 10 | pNM 481 | pNMGF7 | 3 | (not yet known) |
| 11 | pNM 480 | pNMGL8 | 37 | |
| 12 | pNM 482 | pNMGF78 | 103 | |
| FP4b | pNM 481 | pNM4b30 | 34 | 283 |
| FP4b | pNM 481 | pNM4b31 | 21 | 292 |

(c) Testing promoters in a transient assay system.

Chicken embryo fibroblast cells (CEFs) seeded in 24-cell tissue culture dishes (Linbro) were infected with fowlpox virus strain HP441 when the cells were 80-90% confluent. At various times after infection DNA was introduced into the cells by a calcium phosphate transfection procedure. The system was optimised with respect to multiplicity of infection, times for DNA transfection and quantity of DNA for transfection, using the plasmid pMM6 which contains the vaccinia 11K promoter fused to the beta-galactosidase gene which was found to express beta-galactosidase activity in this transient assay system in FPV-infected cells. Although these was variation between individual experiments, the technique adopted, when internally controlled with pMM6 as a positive, and plasmid containing irrelevant sequences as a negative, worked consistently.

Cells in 24-well plates were infected at 1 pfu of FPV HP441 per cell. Precipitates were prepared in 96-well plates by adding ingredients in the following order: pNM plasmid DNA (0.2 μg-5 μg) plus 1 μg FPV "helper" DNA, 100 μl HEPES buffered saline (pH 7.12), and finally 7 μl of 2M CaCl₂. The plates were tapped gently to mix the contents, then left at room temperature for 20-30 minutes until a just visible, fine precipitate developed. 24-well plates of cells to be transfected were pre-washed with HEPES-buffered saline at room temperature, then the appropriate precipitate added at 4 or 20 hours after infection of the cells. After 30 minutes at room temperature the excess precipitate was removed and 0.5 ml 199 medium containing 5% CS was added. The transfected cells were reincubated as normal for a further 48 hours.

Beta-galactosidase activity was assayed as follows.

The tissue culture medium was carefully removed by aspiration, and the cells resuspended in 50 μl of 0.25M TRIS-HCl pH 7.5, 5 mM dithiothreitol (DTT). The resuspended cells were freeze-thawed three times then transferred to 96-well plates for assay of beta-galactosidase content. To each lysate was added 1 μl of a buffer containing 60 mM Na$_2$HPO$_4$, 40 mM and NaH$_2$PO$_4$. 10 mM KCl, 1 mM MgCl$_2$, 50 mM 2-mercaptoethanol and 100 μl of 2 mg/ml orthonitrophenylgalactose (ONPG) in 60 mM Na$_2$HPO$_4$, 40 mM NaH$_2$PO$_4$. ONPG is a colorimetric substrate for beta-galactosidase which changes from colourless to yellow. The assay was incubated for up to 2 hours at 37° C. until colour developed, then 100 μl of 2M Na$_2$CO$_3$ was added to stop the reaction. The intensity of the yellow colour was determined by measured the absorbance of 405 nm of each well in a ELISA plate reader.

RESULTS OF PROMOTER ASSAYS

The sequences from in front of the eleven largest major ORFs from pMH23 and from in front of the FP4b gene (see above) have been cloned into translational fusion vectors (vectors containing the lacZ gene) and their activity as promoters measured in a transient assay system. Table 2 above gives a list of these constructs. Of the 14 FPV promoter constructs tested, five were found consistently to have promoter activity. These were the two FP4b constructs, the ORF8 (13.2K gene) promoter, the ORF5 (12.5K gene) promoter and the ORF10 (33.0K gene) promoter. All these are promoters of the invention. The remainder of the constructs had lower levels of activity. Table 3 shows the results of three experiments. An asterisk denotes a construct containing a promoter of the invention.

TABLE 3

Measurement of promoter strength in assay for beta-galactosidase using a colorimetric substrate (* = according to the invention) OPTICAL DENSITIES at 405 nm

| ORF ref. | Final Construct Vector ref. | Amount of DNA added 20 hours p.i. | | |
|---|---|---|---|---|
| | | 0.2 μg | 1.0 μg | 5.0 μg |
| Experiment A. | | | | |
| 1 | pNMGF32 | 0.011 | 0.057 | 0.04 |
| 2 | not done | | | |
| 3 | pNMGE23 | 0.013 | 0.066 | 0.024 |
| 4 | not done | | | |
| *5 | pNMGK4 | 0.026 | 0.098 | 0.103 |
| 6 | pNMGF6 | 0.047 | 0.093 | 0.057 |
| 7 | pNMGB86 | 0.031 | 0.079 | 0.027 |
| 7 | pNMSAU4 | 0.024 | 0.065 | 0.016 |
| *8 | pNMGC44 | 0.033 | 0.129 | 0.248 |
| *10 | pNMGF7 | 0.027 | 0.071 | 0.138 |
| 11 | pNMGL8 | 0.03 | 0.052 | 0.062 |
| 12 | pNMGF78 | 0.04 | 0.063 | 0.069 |
| *FP4b | pNM4b30 | 0.065 | 0.197 | 0.310 |
| *FP4b | pNM4b30 | 0.057 | 0.203 | 0.260 |

| ORF ref. | Final Construct Vector ref. | Amount of DNA added 4 hours p.i. | | |
|---|---|---|---|---|
| | | 0.2 μg | 1.0 μg | 5.0 μg |
| Experiment B (DNA added earlier than in A) | | | | |
| 1 | pNMGF32 | 0.00 | 0.01 | 0.05 |
| 2 | pNMGJ13M | 0.03 | 0.00 | 0.02 |
| 3 | pNMGE23 | 0.02 | 0.03 | 0.06 |
| 4 | pNMGA5 | 0.03 | 0.39 | 0.08 |

TABLE 3-continued

Measurement of promoter strength in assay for beta-galactosidase using a colorimetric substrate (* = according to the invention)
OPTICAL DENSITIES at 405 nm

| | | | | |
|---|---|---|---|---|
| *5 | pNMGK4 | 0.18 | 0.59 | 0.89 |
| 6 | pNMGF6 | 0.01 | 0.01 | 0.02 |
| 7 | pNMGB86 | 0.00 | 0.00 | 0.04 |
| 7 | pNMSAU4 | 0.03 | 0.04 | 0.03 |
| *8 | pNMGC44 | 0.11 | 0.22 | 0.71 |
| *10 | pNMGF7 | 0.08 | 0.10 | 0.16 |
| 11 | pNMGL8 | 0.06 | 0.05 | 0.04 |
| 12 | pNMGF78 | 0.05 | 0.05 | 0.07 |
| *FP4b | pNM4b30 | 0.35 | 0.27 | 0.58 |
| *FP4b | pNM4b31 | 0.28 | 0.32 | 0.44 |
| Whole pMH23 | | 0.01 | 0.02 | 0.02 |
| No DNA | | 0.01 | 0.01 | 0.01 |
| Experiment C (duplicate of B) | | | | |
| 1 | pNMGF32 | 0.00 | 0.07 | 0.04 |
| 2 | pNMGJ13M | 0.02 | 0.07 | 0.08 |
| 3 | pNMGE23 | 0.06 | 0.01 | 0.00 |
| 4 | pNMGA5 | 0.05 | 0.00 | 0.09 |
| *5 | pNMGK4 | 0.07 | 0.13 | 0.74 |
| 6 | pNMGF6 | 0.05 | 0.05 | 0.02 |
| 7 | pNMGB86 | 0.05 | 0.07 | 0.08 |
| 7 | pNMSAU4 | 0.04 | 0.05 | 0.05 |
| *8 | pNMGC44 | 0.05 | 0.18 | 0.65 |
| 10 | pNMGF7 | 0.02 | 0.05 | 0.31 |
| 11 | pNMGL8 | 0.03 | 0.06 | 0.09 |
| 12 | pNMGF78 | 0.03 | 0.03 | 0.02 |
| *FP4b | pNM4b30 | 0.28 | 0.30 | 1.24 |
| *FP4b | pNM4b31 | 0.11 | 0.25 | 1.18 |
| Whole pMH23 | | 0.10 | 0.06 | 0.10 |
| No DNA | | 0.03 | 0.04 | 0.04 |

For experiment A the DNA was added 20 hours post infection, and for experiment B and C, which are essentially duplicates of each other, the DNA was added 4 hours post infection. It is interesting to notice that some of the promoters appear to have higher activity when added early after infection. For example at 4 hours post infection the ORF5 promoter can give higher levels of activity than the ORF8 promoter, whereas when it is added late it has lower levels. It maybe the ORF5 is an early promoter which does not function well when added relatively late in infection. The ORF10 promoter, on the other hand, seems to function between when added later in infection. Both the FP4b constructs give consistently high levels.

Part of the sequences of the constructs used to test the FP4b, the ORF8 (13.2K), ORF5 (12.5K) and ORF10 (33K) promoters are shown below. Each sequence starts and finishes with DNA from the pNM vector involved, and shows how the intervening sequence is made up from fowlpox sequences plus M13 DNA. Two of the putative promoter sequences have been tested out in two separate constructs, each having different numbers of ORF amino acid coding sequence in the fused product. These are the FP4b30/FP4b31 pair and the pNMGB86/pNMSAU4 pair. In both cases the levels of promoter activity between the two different members of the pair were very similar, indicating that the length of fowlpox gene in the fused product is not critical.

Part of the sequence of pNM4b30.

```
————————————————————— pNM481 sequence —————————> <— M13 sequence ———
GCGCAACTGTTGGGAAGGGCGATCGGTGCGGGCCTCTTCGCTATTACGCCAGAATTCGAG
    10        20        30        40        50        60

——————>  <————————————— start of fowlpox (FP) sequence —————————————
CTCGCCCTATTAACATTGCCTAGTAGTACTCCACTTTGGATAAGAAATCTGCATGATAAA
    70        80        90       100       110       120

————————  ——  ——  ——
TATATTGATATCCTACCACCTATTAAAGTACCATTATCTAATAGCAATAAGATAGATAAA
   130       140       150       160       170       180

CAAATGTTTTTTGATGAAGTTATTACGTGGATAAATATATATCTTCAGGAAAAGGGTATT
   190       200       210       220       230       240

ATGTTACCAGATGATATAAGAGAACTCAGAGATGCTATTATTCCTTAACTAGTTACGTCT
   250       260       270       280       290       300

|————— start of FP4b gene
CTTTAGGTACTTATTTTGATACGTTACAAGTAAAAAACTATCAAATATAAATGGAATCTG
                                                 Met Glu Ser Asp
   310       320       330       340       350       360

ATTCTAATATAGCCATTGAAGAAGTTAAATATCCTAATATTTTATTAGAACCTGTTTACT
 Ser Asn Ile Ala Ile Glu Glu Val Lys Tyr Pro Asn Ile Leu Leu Glu Pro Val Tyr Tyr
   370       380       390       400       410       420 end of FP sequence ——————> <————— sequence from M13mp10 ———
ATAATAACCTAGAAGTAATAGGATCTCATTTACGGGGATCCTCTAGAGTCGACCTGCAGC
 Asn Asn Leu Glu Val Ile Gly Ser His Leu Arg Gly Ser Ser Arg Val Asp Leu Gln Pro
   430       440       450       460       470       480

——————>  <————————— sequence from pNM481 (lacZ gene) ——————————— etc ...
CCAAGCTTGCTCCCCTGGCCGTCGTTTTACAACGTCGTGACTGGAACCCTGGCGTT
 Lys Leu Ala Pro Leu Ala Val Val Leu Gln Arg Arg Trp Asn Pro Gly Val
   490       500       510       520       530
```

-continued

Part of the sequence of pNM4b31.

———————————————— pNM481 sequence ————————————————→ ←— M13 sequence
GCGCAACTGTTGGGAAGGGCGATCGGTGCGGGCCTCTTCGCTATTACGCCAGAATTCGAG
         10        20        30        40        50        60

————→ ←———————————— start of fowlpox (FP) sequence ————————————————
CTCGCCCAGTCACAAGTATTAACATTGCCTAGTAGTACTCCACTTTGGATAAGAAATCTG
         70        80        90       100       110       120

CATGATAAATATATTGATATCCTACCACCTATTAAAGTACCATTATCTAATAGCAATAAG
        130       140       150       160       170       180

ATAGATAAACAAATGTTTTTTGATGAAGTTATTACGTGGATAAATATATATCTTCAGGAA
        190       200       210       220       230       240

AAGGGTATTATGTTACCAGATGATATAAGAGAACTCAGAGATGCTATTATTCCTTAACTA
        250       260       270       280       290       300

| —start opf FP4b gene
GTTACGTCTCTTTAGGTACTTATTTTGATACGTTACAAGTAAAAAACTATCAAATATAAA
                                                              Met
        310       320       330       340       350       360 end of FP sequence ——————
TGGAATCTGATTCTAATATAGCGATTGAAGAAGTTAAATATCCTAATATTTTATTAGAAC
Glu Ser Asp Ser Asn Ile Ala Ile Glu Glu Val Lys Tyr Pro Asn Ile Leu Leu Glu Pro
        370       380       390       400       410       420

————→ ←———————— sequence from M13mp10 ————————→ ←———————— sequence from pNM481
CTGGGGGATCCTCTAGAGTCGACCTGCAGCCCAAGGTTGCTCCCCTGGCCGTCGTTTTAC
Gly Gly Ser Ser Arg Val Asp Leu Gln Pro Lys Leu Ala Pro Leu Ala Val Val Leu Gln
        430       440       450       460       470       480

(lacZ) ———————————————————————— etc. . .
AACGTCGTGACTGGGAAAACCCTGGCGTT
Arg Arg Asp Trp Glu Asn Pro Gly Val
        490       500

Part of the sequence of pNMGC44.

←———————————————— pNM482 sequence ————————————————→ ←—M13 sequence —
GCGCAACTGTTGGGAAGGGCGATCGGTGCGGGCCTCTTCGCTATTACGCCAGAATTCGAG
         10        20        30        40        50        60

————→ ←———————————— start of fowlpox (FP) sequence ————————————————
CTCGCCCTGAACTTTCCAGAATCTAATAATTCTTCCACTTTAACAACGTCTCCTTCTTCC
         70        80        90       100       110       120

ACGGCCTCATGCAATTCAGATTCTATATCCGGATAGTTATAATCGGGATAAGTGTTGTAA
        130       140       150       160       170       180

CTCATCAGTAATTTAATCATTTCAACATCTCTAAGTCTGACGGCCATCTTTATAGGCGAG
        190       200       210       220       230       240

TATCCGTTGATAGTAAAATTCGGATTGATGTAAGAATCCAACAGGCGTCTAGCCACATCC
        250       260       270       280       290       300

AGTTCTCCAAAGAGAATAGCATTGCAAAGTTCTACACGATCCATTGTATAATATAGGTGT
        310       320       330       340       350       360

TCAACACCTCTCGATATATCATTATTTGTTTTTTTCAATTTTATTATAAGTAGTTTGAATG
        370       380       390       400       410       420

| ———————— start of ORF 8 gene
CATTTTTAAGTTTAATAAATCTTGATAAAGTATATTTAAAAAATGGAGGAGGGTAAACCG
                                              Met Glu Glu Gly Lys Pro
        430       440       450       460       470       480

———→ >< ——————— sequence from M13mp10 ——————→ <—
CGACGTAGTAGCGCAGTATTATGGGGGGATCCTCTAGAGTCGACCTGCAGCCCAAGCTTC
Arg Arg Ser Ser Ala Val Leu Trp Gly Asp Pro Leu Glu Ser Thr Cys Ser Pro Ser Phe
         490              500              510              520              530              540

——————————— sequence from pNM482 (lacZ gene) ——————————— etc...
GATCCCCTGGCCGTCGTTTTACAACGTCGTGACTGGGAAAACCCTGGCGTT
Asp Pro Leu Ala Val Val Leu Gln Arg Arg Asp Trp Glu Asn Pro Gly Val
         550              560              570              580              590

Part of the sequence of pNMGK4.

————————————— pNM482 sequence ————————————→ <— M13 sequence —
GCGCAACTGTTGGGAAGGGCGATCGGTGCGGGCCTCTTCGCTATTACGCCAGAATTCGAG
         10               20               30               40               50               60

——→ <——————————— start of fowlpox (FP) sequences ———————————
CTCGCCCGAATAAAGATTCTAAATCTACGCACGTAATAAACCAAATATACTAAAATATAA
         70               80               90              100              110              120

——————
AATTATGCCGCGGGATGATAAGATACTTCAGATGATCGTGATGAACTATATTTATTAATT
         130              140              150              160              170              180

GGCAATACTTAAAAATAATGTTTATAACATATGTAAATATAATAAACAATAATTTAGATT
         190              200              210              220              230              240

| ————— start of ORF 5 gene ————→ <—— sequence from M13mp10 ——
TTTAAAATGATAATACGTAGGAATAATAAAGCTCTTGGGGATCCTCTAGAGTCGACCTGC
         Met Ile Ile Arg Arg Asn Asn Lys Ala Leu Gly Asp Pro Leu Glu Ser Thr Cys
         250              260              270              280              290              300

——————→ <——————— sequence from pNM482 (lacZ gene) ———————
AGCCCAAGCTTCGATCCCCTGGCCGTCGTTTTACAACGTCGTGACTGGGAAAACCCTGGC
Ser Pro Ser Phe Asp Pro Leu Ala Val Val Leu Gln Arg Arg Asp Trp Glu Asp Pro Gly
         310              320              330              340              350              360

—— etc...
GTT
Val

Part of the sequence of pNMGF7.

————————————— pNM481 sequence ————————————→ <— M13 sequence —
GCGCAACTGTTGGGAAGGGCGATCGGTGCGGGCCTCTTCGCTATTACGCCAGAATTCGAG
         10               20               30               40               50               60

——→ <——————————— start of fowlpox (FP) sequence (exact left end unknown) —
CTCGCCCXXX XXXXXXXXXX XXXXXXXXX XXXXXXXCTGACAAAATTAGATGACATGAT
         70               80               90              100              110              120

—— FP sequence continued ——————————————————————
CTTACGAAATCTACTACTACAAAATGAGACAAATAATATTAAAAATTGTAAAAAACAGTA
         130              140              150              160              170              180

ATATAAATATGATAAGAAAATGTGTAAAAAAGCTAGGAAACGCGGTCTATTAACGATAGC
         190              200              210              220              230              240

TTTCACTATATTGTTATTTGTTATTATTTTAGTAGATATAGACAGAGATAGATATTTAGT
         250              260              270              280              290              300

AAGGTGTGGTAAAGACTGGTTAGAATTCGATAATTTATGTTATTTTATTTCCGAAAATAA
         310              320              330              340              350              360

GTTAAGTTGGGATGATAGCATGATGGTATGTGATAATCTTGGCGGTGGGAATAATATTAA
         370              380              390              400              410              420

CATAAATACGAATAGTGGCTTATTAAATACATCTAAGGACTATTGGATAAAAATAGTAGA
         430              440              450              460              470              480

CGAACTAGATTGTACAAATATTAATATGTGTAATTTCTTATATAGTAATATAGTAGGATG
         490              500              510              520              530              540

```
                                        -continued
TGATATATGCACCATAGAAAAATTTTATATTTGTATAAAACCGATAAATAAAATAAACTT
     550         560         570         580         590         600

|—ORF 10—>  <—sequence from M13mp10 —
ATTTAGTTACTTTGTAGAGTATACTAAATAATAATGAAATTTAGGGGATCCTCTAGAGTC
                                    Met Lys Phe Arg Gly Ser Ser Arg Val
     610         620         630         640         650         660

————————————————>  <———————sequence from pNM481 (lacZ gene)———————
GACCTGCAGCCCAAGCTTGCTCCCCTGGCCGTCGTTTTACAACGTCGTGACTGGGAAAAC
Asp Leu Gln Pro Lys Leu Ala Pro Leu Ala Val Val Leu Gln Arg Arg Asp Trp Glu Asn
     670         680         690         700         710         720

——————————etc. . .
CCTGGCGTT
Pro Gly Val
```

INSERTION OF GENES INTO FOWLPOX VIRUS

Foreign genes are introduced into the virus by a process of homologous recombination. This process has been described in the literature in detail for vaccinia virus and an analogous procedure can be used for fowlpox virus.

1. Infection with virus and transfection of DNA

25 $cm^2$ bottles of CEF cells at about 80% confluence are infected with about $10^7$ pfu (about 3 pfu/cell) of an attenuated strain of fowlpox virus in 1 ml of serum-free medium. The bottles are incubated at 37° C. for 2 hours with occasional gentle agitation then 5 ml of 199 medium (Gibco) with 5% calf serum are added and the cells are incubated for a further 2 hours at 37° C.

30 minutes before this 2 hours is up the DNA/$CaPO_4$ precipitates are prepared. 20 μg of plasmid DNA, which contains a "type 1 construct" and therefore includes non-essential regions of FPV plus 2 μg of fowlpox "helper" DNA are added to 1 ml of HEPES buffered saline (HBS) pH 7.12 in a plastic bijou (HBS is 0.818% NaCl (w/v), 0.594% HEPES (w/v), 0.02% $Na_2HPO_4$ anhydrous (w/v), adjusted to pH 7.12 with 1M NaOH). 66 μl of 2M $CaCl_2$ is added slowly down the side of the bijou. This is left at room temperature for 20 to 30 minutes for a fine precipitate to form.

After the 2 hours incubation, the cells are washed twice with HBS at room temperature and the precipitate is gently added to the cells. This is left at room temperature for 40 minutes and then 5 ml of 199 medium with 5% calf serum is added and the cells are incubated at 37° C. for 3 to 4 hours. The medium is then changed for fresh medium.

2. Detection of recombinants

After the virus has been allowed to grow in the cells for 3-5 days (this is when a complete cytopathic effect can be seen) the cells plus supernatant are harvested and freeze thawed three time. The progeny virus is then plaqued on CEF cells at about 500-1000 plaques per 10 cm petri dish and an overlay of medium containing 1% low gelling temperature agarose is added. The plaques are then lifted onto nitrocellulose and probed with DNA from the foreign gene which is being inserted into the fowlpox virus by the method of L. Villareal et al., Science 196, 183-185 (1977). Plaques which are found to light up with the probe are picked from the agarose overlay (which has been stored at 4° C.), freeze-thawed three times and replaques. The plaques are then probed again with the foreign DNA to confirm that the recombinant virus has been isolated successfully from the agarose overlay.

INFECTION OF CHICKENS WITH THE RECOMBINANT VIRUS

Twenty two chicks, 5 days, oil, are placed in a container (46×46×58 $cm.^3$) A spray gun is used to create a fine aerosol using 80 ml. water containing $1.5\times10^8$ p.f.u. of virus grown in chicken embryo fibroblast cells. This vaccination is repeated when the chicks are 26-days old.

EXAMPLE 2

Promoters are signals in the viral DNA which direct transcription of RNA. Strong promoters will therefore direct transcription of greater amounts of RNA than weak promoters. This is used as a way of identifying efficient promoters. If radiolabelled viral RNA is hybridised to restriction fragments of viral DNA, immobilised on a nitrocellulose filter, particular regions of the virus containing strong promoters might be identified. For late RNA this might be expected to be difficult since late RNA transcripts are known to run well past the end of their genes, possibly into adjacent restriction fragments, hence confusing any attempts at mapping. However for early RNA it should be a useful approach. ('Early' RNA is RNA made before DNA replication and 'late' RNA is made after DNA replication, by definition. RNA made even earlier, i.e. before protein synthesis, can be referred to as 'immediate early RNA'). A convenient method of making radiolabelled RNA of the immediate early class is to use a in vitro system containing purified virus, deoxynucleoside triphosphates, one of which is radioactively labelled, and a suitable buffer. This has been described for vaccinia virus by S. Venkatesan & B. Moss, J. Virology 37 738-747 (1981) and it is found that the RNA produced in vitro (i.e. in a test tube) in this manner has the same pattern as that made in vivo (i.e. in tissue culture).

METHODS

Virus purification

Virus was grown in chick embryo fibroblast (CEF) cells and purified as follows: Forty 75 $cm^2$ flasks of CEFs were infected with $5\times10^6$ pfu/flask of PP9 (a plaque-purified isolate of HP440). The flasks were incubated at 37° C. for 5 days. The cells were then shaken off into the medium and then spun down at 7,000 rpm for 15 minutes. The supernatant containing the virus was then centrifuged at 15,000 rpm for 30 minutes at 4°

C. The virus pellets were pooled and resuspended in 40 ml phosphate-buffered saline (PBS). This was layered onto a cushion of 10 ml of 35% (w/v) sucrose and centrifuged at 15,000 rpm for 30 minutes. The viral pellet was then resuspended in 1 ml of PBS. This was then layered onto a 20–50% (w/v) sucrose gradient and centrifuged at 15,000 rpm for 30 minutes. The two viral bands were collected, pooled, layered onto two 20–60% metrizamide gradients (about 1 ml per gradient) and centrifuged at 30,000 rpm for 18–20 hours. The viral band was then collected (1 ml per gradient).

In vitro synthesis of labelled RNA. (based on the method of S. Venkatesan & B. Moss, 1981 loc. cit.) $10^9$ pfu of purified virus particles from the above procedure were used as follows to produce labelled RAN. The virus solution was made to 0.05% Nonidet P-40 (NP-40) and left on ice for 1 hour. This was then added to a solution containing 50 mM Tris-HCl (pH 8.5), 10 mM dithiothreitol, 5 mM ATP, 1 mM each of GTP and CTP, 10 mM $MgCl_2$, 100 $\mu$M S-adenosylmethionine (AdoMet), and 100 $\mu$Ci of $^{32}$P-labelled UTP, the total volume being 5 ml. After 30 minutes at 37° C. fresh AdoMet (the same amount again) was added and the reaction incubated for a further 30 minutes. The reaction was terminated by addition of EDTA to 10 mM, and the tubes were placed on ice. The virus was then pelleted by centrifugation at 30,000 rpm for 30 minutes, the labelled RNA being contained in the supernatant. To the supernatant was added sodium dodecyl sulphate (SDS) to a final concentration of 0.25% and the mixture extracted with an equal volume of phenol saturated in TE (10 mM TRIS-HCl, pH 7.5, 1 mM EDTA). The aqueous layer was removed and extracted with diethyl ether and the RNA precipitated by addition of 1/10 volume of 3M sodium acetate and 2.5 volumes of ethanol. The RNA was spun down at 15,000 rpm for 10 minutes and the pellet resuspended in 4 ml of guanidine thiocyanate solution (6M guanidine thiocyanate, 0.5% sodium N-laurylsarcosine. 5 mM sodium citrate, 0.1M 2-mercaptoethanol). This was layered onto a 1 ml cushion of CsCl/EDTA (5.7M CsCl, 0.1M EDTA) and centrifuged at 38,000 rpm for 18–20 hours at 18° C. to pellet the RNA. The supernatant was carefully removed and discarded and the RNA pellet resuspended in 500 $\mu$l of diethyl pyrocarbonate-treated water.

Hybridisation to DNA.

a) Restriction digests

An EcoRI digest of FPV DNA, and a BamHI/EcoRI digest of the 11.2 kb BamHI clone were separated on 0.9% agarose gels. The DNA was transferred to nitrocellulose filters by Southern blotting. Single-stranded preparations of M13 clones from the 11.2 kb fragment were spotted onto nitrocellulose and baked for 2 hours at 80° C. in a vacuum (1/10 of the DNA from a 1 ml culture). The filters were prehybridised in 10 ml of 5×SSC (SSC is 0.15M NaCl, 0.015M Sodium-citrate) for 2 hours at 60° C. The suspension of labelled RNA being used as a probe was boiled for 3 minutes before addition to the filters. The probe and filters were incubated, with shaking, at 60° C. for 18–20 hours. The filters were washed in 2×SSC, 0.1% SDS, at 42° C. for 30 minutes, then in 0.1×SSC, 0.1% SD Sat 25C for 30 minutes, and thereafter exposed to X-ray film.

RESULTS

The labelled viral RNA was found to hybridise strongly to only two EcoRI fragments in the digest of FPV DNA. One was 790 bp long and the other was 3830 bp. (Some larger sized bands, particularly in the region of about 6,000 bp, hybridised weakly). The RNA also hybridised to a 3830 bp band in the EcoRI/BamHI digest of the 11.2 kb BamHI fragment. Labelled EcoRi FPV DNA fragments of sizes 790 bp and 3830 bp, purified from an agarose gel, were used to probe, by the well-known method of Grunstein & Hogness, an EcoRI library of FPV DNA fragments cloned into puC13. Several pUC13 clones were thus identified which were also probed with the labelled in vitro RNA. The resulting group of pUC13 clones proved to fall into two categories, those with viral inserts of 790 bp in size and those with inserts of 3830 bp in size. The 3830 bp-sized clones were probed with labelled 3830 bp fragment from the 11.2 kb BamHI fragment (nucleotides 6162 to 9992 : the EcoRI sites are underlined) and were found to be the same. The 3830 bp fragment includes the whole of the strongly promoted ORF8 and ORF10 genes.

b) M13 clones from the 11.2 kb fragment

A series of single-stranded M13 clones from the 11.2 kb BamHI fragment were spotted onto nitrocellulose. Clones were chosen so that each major open reading frame (ORF) in the fragment was represented by one clone in the same orientation as the expected RNA from that ORF (i.e. unable to hybridise to the RNA) and one clone in the opposite orientation (i.e. expected to hybridise to RNA from that ORF). The clones were as follows.

| ORF | Clone reference | Nucleotide No. Start | Finish | Expected to hybridise? (+ = YES; − = NO) |
|---|---|---|---|---|
| 1. (416–1674) | GC47 | 407 | 725* | + |
|  | GC50 | 860 | 545* | − |
| 2. (2166–2671) | GB53 | 2682 | 2887* | + |
|  | GF18 | 2639 | 2581* | − |
| 3. (4055–3606) | GD45 | 3706 | 3918* | − |
|  | GA28 | 3887 | 3627* | + |
| 4. (4170–4594) | GF48 | 4096 | 4305* | + |
|  | GF95 | 4481 | 4228* | − |
| 5. (5138–4821) | GF73 | 5078 | 5404* | − |
|  | GG2 | 5041 | 4727* | + |
| 6. (5974–5519) | GE3 | 5604 | 5821* | − |
|  | GF110 | 5824 | 5601* | + |
| 7. (7906–6674) | GC59 | 7000 | 7290* | − |
|  | GC61 | 7283 | 7005* | + |
| 8. (8025–8376) | GF74 | 7977 | 8238 | + |
|  | GB150 | 8351 | 8085* | − |
| 9. (8632–8837) | MFP344 | 8781 | 8980* | + |
|  | GJ24 | 8785 | 8584 | − |
| 10. (9686–8844) | GC43 | 9277 | 9499* | − |
|  | GB84 | 9495 | 9230* | + |
| 11. (10120–9689) | GC45 | 9813 | 10066* | − |
|  | GB161 | 10107 | 9828 | + |
| 12. (10705–10139) | GB64 | 10359 | 10571* | − |
|  | GF21 | 10584 | 10276* | + |

*This is not the actual end of the clone, but merely the point up to which it was sequenced.

RESULTS

Only the following clones hybridised to the in vitro RNA:

| | |
|---|---|
| GG2 | very strongly (ORF 5 promoter) |
| GC61 | weakly |
| GJ24 | very strongly (despite the fact that it is a "same orientation" clone) |
| GB84 | moderately strongly (ORF 10 promoter) |

These results give a reasonable confirmation of the use of the RNA transcription method of identifying an immediately early strong promoter. Thus, the clones containing the ORF 5 and ORF 10 promoters hybridised strongly to the mRNA. No signal was obtained from the clone containing the ORF 8 promoter, presumably because it does not act at the immediate early stage. The strong hybridisation of GJ24 (nucleotides 8785 to 8584) is probably a result of the mRNA transcribed for the ORF 10 gene (nucleotides 9686 to 8844) running beyond the end of the gene at 8844, well into the DNA which encodes ORF 9 (8632 to 8835).

It follows that when an immediate early promoter is required, the ORF 5 and ORF 10 promoters appear likely to be good choices.

We claim:

1. An isolated DNA consisting essentially of the promoter sequence which is located immediately 5' to an open reading frame in the fowlpox virus genome, said open reading frame being selected from the group consisting of:
   (1) The FB4b gene which is fowlpox virus encodes a protein of about 657 amino acids in a sequence beginning Met Glu Ser Asp Ser Asn Ile Ala Ile Glu Glu Val Lys Tyr Pro Asn Ile Leu Leu Glu, (2) The BamHI fragment ORF8 gene encoding a protein of about 116 amino acids in a sequence beginning Met Glu Glu Gly Lys Pro Arg Arg Ser Ser Ala Val Leu Trp Met Leu Ile Pro Cys Gly, (3) The BamHI fragment ORF5 gene encoding a protein of about 105 amino acids in a sequence beginning Met Ile Ile Arg Arg Asn Asn Lys Ala Leu Gly Ser Val Met Ser Asp Phe Ile Lys Thr, and (4) The BamHI fragment ORF10 gene encoding a protein of about 280 amino acids in a sequence beginning Met Lys Phe Lys Glu Val Arg Asn Thr Ile Lys Lys Met Asn Ile Thr Asp Ile Lys Ile.

2. DNA according to claim 1, wherein the promoter sequence is of length up to 150 nucleotides.

3. DNA according to claim 2, wherein the promoter sequence is of length up to 100 nucleotides.

4. DNA according to claim 2, wherein said 150 nucleotides are selected from the group consisting of:

```
FP4b (5')  TATTACGTGG ATAAATATAT ATCTTCAGGA AAAGGGTATT ATGTTACCAG
           ATGATATAAG AGAACTCAGA GATGCTATTA TTCCTTAACT AGTTACGTCT
           CTTTAGGTAC TTATTTTGAT ACGTTACAAG TAAAAAACTA TCAAATATAA
                                                                (3'),

ORF8 (5')  AGAATAGCAT TGCAAAGTTC TACACGATCC ATTGTATAAT ATAGGTGTTC
           AACACCTCTC GATATATCAT TATTTGTTTT TTCAATTTTA TTATAAGTAG
           TTTGAATGCA TTTTTAAGTT TAATAAATCT TGATAAAGTA TATTTAAAAA
                                                                (3'),

ORF5 (5')  TAAACCAAAT ATACTAAAAT ATAAAATTAT GCCGCGGGAT GATAAGATAC
           TTCAGATGAT CGTGATGAAC TATATTTATT AATTGGCAAT ACTTAAAAAT
           AATGTTTATA ACATATGTAA ATATAATAAA CAATAATTTA GATTTTTAAA
                                                                (3'), and ORF10 (5') ACTAGATTGT ACAAATATTA ATATGTGTAA TTTCTTATAT AGTAATATAG
           TAGGATGTGA TATATGCACC ATAGAAAAAT TTTATATTTG TATAAAACCG
           ATAAATAAAA TAAACTTATT TAGTTACTTT GTAGAGTATA CTAAATAATA
                                                                (3')
```

5. Recombinant DNA comprising the promoter sequence which is located immediately 5' to an open reading frame in the fowlpox virus genome, said open reading frame being selected from the group consisting of:
   (1) The FP4b gene which in fowlpox virus encodes a protein of about 657 amino acids in a sequence beginning Met Glu Ser Asp Ser Asn Ile Ala Ile Glu
   Glu Val Lys Tyr Pro Asn Ile Leu Leu Glu (2) The BamHI fragment ORF8 gene encoding a protein of about 116 amino acids in a sequence beginning Met Glu Glu Gly Lys Pro Arg Arg Ser Ser Ala Val Leu Trp Met Leu Ile Pro Cys Gly, (3) The BamHI fragment ORF5 gene encoding a protein of about 105 amino acids in a sequence beginning Met Ile Ile Arg Arg Asn Asn Lys Ala Leu Gly Ser Val Met Ser Asp Phe Ile Lys Thr, and (4) The BamHI fragment ORF10 gene encoding a protein of about 280 amino acids in a sequence beginning Met Lys Phe Lys Glu Val Arg Asn Thr Ile Lys Lys Met Asn Ile Thr Asp Ile Lys Ile, transcribably linked to a foreign gene.

6. Recombinant DNA according to claim 5, wherein the promoter sequence is of length up to 150 nucleotides.

7. Recombinant DNA comprising a non-essential region (NER) sequence of fowlpox virus interrupted by DNA according to claim 5.

8. A recombinant cloning vector comprising DNA according to claim 7 and vector sequence.

* * * * *